US008753829B2

(12) United States Patent
Alper

(10) Patent No.: US 8,753,829 B2
(45) Date of Patent: Jun. 17, 2014

(54) MONOCLONAL ANTIBODIES AGAINST HER2 ANTIGENS, AND USES THEREFOR

(71) Applicant: Alper BioTech, LLC, Rockville, MD (US)

(72) Inventor: Özge Alper, Bethesda, MD (US)

(73) Assignee: Alper Biotech, LLC, Rockville, MD (US)

( * ) Notice: Subject to any disclaimer, the term of this patent is extended or adjusted under 35 U.S.C. 154(b) by 0 days.

(21) Appl. No.: 13/705,048

(22) Filed: Dec. 4, 2012

(65) Prior Publication Data

US 2013/0089873 A1  Apr. 11, 2013

Related U.S. Application Data

(62) Division of application No. 13/087,351, filed on Apr. 14, 2011, now Pat. No. 8,349,585.

(60) Provisional application No. 61/324,490, filed on Apr. 15, 2010.

(51) Int. Cl.
*G01N 33/574* (2006.01)

(52) U.S. Cl.
USPC ............ 435/7.23; 435/7.1; 435/7.2; 530/350; 530/387.1; 530/387.3; 530/387.7; 530/388.2; 530/388.8; 530/391.3; 436/64; 436/501

(58) Field of Classification Search
USPC ...................... 435/7.1, 7.2, 7.23; 436/64, 501; 530/350, 387.1, 387.3, 387.7, 388.2, 530/388.8, 391.3
See application file for complete search history.

(56) References Cited

U.S. PATENT DOCUMENTS

| 2009/0285837 A1 | 11/2009 | Kao et al. |
| 2011/0256056 A1 | 10/2011 | Alper |
| 2013/0243760 A1 | 9/2013 | Alper |

FOREIGN PATENT DOCUMENTS

| JP | 3-191865 | 8/1991 |
| WO | WO 96/32480 | 10/1996 |
| WO | WO 01/09187 | 2/2001 |
| WO | WO 2006/087637 | 8/2006 |
| WO | WO 2008/019290 | 2/2008 |

OTHER PUBLICATIONS

Alper et al., "The Presence of *c-erb*B-2 Gene Product-related Protein in Culture Medium Conditioned by Breast Cancer Cell Line SK-BR-3," *Cell Growth & Differentiation*, 1: 591-599 (Dec. 1990).
Alper BioTech, LLC, "Alper Biotech HER-2 IHC Kit," product summary released Apr. 17, 2010, Catalog No. AB11, 4 pages.
Alper BioTech, LLC, "Alper Biotech Tissue Diagnostix—Breast Cancer," poster, Apr. 17, 2010, 1 page.
Oncogene Science, "510(k) Summary for the Oncogene Science Diagnostics, Inc. Manual HER-2/neu Microtiter ELISA," 510(k) No. K994112, Sep. 29, 2000.
College of American Pathologists, "HER2 Immunohistochemistry, Tissue Microarray Survey," kit instructions, original ship date Apr. 26, 2010.
Bayer Corporation, "Premarket Notification—510(k) ADVIA Centaur HER- 2/neu Immunoassay," 510(k) No. K024017, Jan. 30, 2003.
Bussolati et al., "A modified Trastuzumab antibody for the immunohistochemical detection of HER-2 overexpression in breast cancer," *British Journal of Cancer*, 92: 1261-1267 (2005).
Glazyrin et al., "Direct Detection of Herceptin/Trastuzumab Binding on Breast Tissue Sections," *Journal of Histochemistry & Cytochemistry*, 55(1): 25-33 (2007).
Hudziak et al., "p185$^{HER2}$ Monoclonal Antibody Has Antiproliferative Effects In Vitro and Sensitizes Human Breast Tumor Cells to Tumor Necrosis Factor," *Molecular and Cellular Biology*, 9(3): 1165-1172 (Mar. 1989).
Li et al., "Characterization and Utilization of Two Novel Anti-erbB-2 Monoclonal Antibodies in Detection of Soluble ErbB-2 for Breast Cancer Prognosis," *Cancer Letters*, 193: 139-148 (2003).
Ross et al., "The HER-2/*neu* Gene and Protein in Breast Cancer 2003: Biomarker and Target of Therapy," *The Oncologist*, 8: 307-325 (2003).
Sapino et al., "Patients with advanced stage breast carcinoma immunoreactive to biotinylated Herceptin® are most likely to benefit from trastuzumab-based therapy: an hypothesis-generating study," *Annals of Oncology*, 18: 1963-1968 (published on line Sep. 4, 2007).
Winston et al., "Her-2/neu Evaluation in Breast Cancer—Are We There Yet?," *Am J Clin Pathol*, 121(Suppl 1): S33-S49 (2004).
Notice of Allowance and Fee(s) Due mailed Oct. 11, 2012, in U.S. Appl. No. 13/087,351.
Office Action mailed Sep. 5, 2013, in U.S. Appl. No. 13/875,196.
Response to Restriction Requirement dated Sep. 13, 2013, in U.S. Appl. No. 13/875,196.
Office Action mailed Sep. 20, 2013, in U.S. Appl. No. 13/875,196.
Reply to Office Action under 37 C.F.R. § 1.111 dated Dec. 12, 2013, in U.S. Appl. No. 13/875,196.

*Primary Examiner* — Stephen Rawlings
(74) *Attorney, Agent, or Firm* — Finnegan, Henderson, Farabow, Garrett & Dunner, LLP

(57) ABSTRACT

The present invention provides and includes monoclonal antibodies (mAbs) preferentially selective for HER2 antigens, hybridoma lines that secrete these HER2 antibodies or antibody fragments, and the use of such antibodies and antibody fragments to detect HER2 antigens, particularly those expressed by cancer cells. The present invention also includes antibodies that are specific for or show preferential binding to a soluble or secreted form of HER2. The present invention also includes an antibody or antibody fragment that is capable of reducing the activity of HER2 in at least one form, including a soluble form or a secreted form. The present invention further includes chimeric antibodies, processes for producing monoclonal and chimeric antibodies or monoclonal or chimeric antibodies, and their therapeutic uses, particularly in the detection of cancer most preferentially in human breast, stomach, and colon. The present invention further includes methods and kits for the immunodetection and immunotherapy of cells for samples which express HER2 antigens.

20 Claims, 16 Drawing Sheets

Objective: 63X representative slide from stomach cancer tissue representative slide from stomach cancer tissue

SEQUENCE LISTING

```
<160> NUMBER OF SEQ ID NOS: 53

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Pro Gly Leu Ala Ala Pro Ser Gln Ser Leu Ser Ile Thr Cys Thr
1               5                   10                  15

Val Ser Gly Phe Ser Leu Thr Ser Tyr Val Ile Ser Trp Val Arg Gln
            20                  25                  30

Pro Pro Gly Lys Gly Leu Glu Trp Leu Gly Val Ile Trp Thr Gly Gly
        35                  40                  45

Gly Thr Asn Tyr Asn Ser Ala Leu Lys Ser Arg Leu Ser Ile Ser Lys
    50                  55                  60

Asp Asn Ser Lys Ser Gln Val Ser Leu Lys Met Asn Ser Leu Gln Thr
65                  70                  75                  80

Asp Asp Thr Ala Arg Tyr Tyr Cys Ala Ser Leu Ser Tyr Asp Gly Phe
                85                  90                  95

Asp Tyr Trp Gly Gln Gly Thr Thr Val Thr
            100                 105

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Ser Leu Thr Ser Tyr Val
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 3

Ile Trp Thr Gly Gly Gly Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ser Leu Ser Tyr Asp Gly Phe Asp Tyr Trp
1               5                   10

<210> SEQ ID NO 5
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ile Leu Met Thr Gln Ser Pro Ala Ile Met Ser Ala Ser Pro Gly Glu
1               5                   10                  15

Lys Val Thr Met Thr Cys Ser Ala Ser Ser Ser Val Ser Tyr Met His
            20                  25                  30

Trp Tyr Gln Gln Lys Ser Gly Thr Ser Pro Lys Arg Trp Ile Tyr Asp
        35                  40                  45

Thr Ser Lys Leu Ala Ser Gly Val Pro Ala Arg Phe Ser Gly Ser Gly
    50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Ser Ser Asn Pro Leu Thr Phe
                85                  90                  95

Gly Ala Gly Thr Lys Leu Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ser Val Ser Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Trp Ser Ser Asn Pro Leu Thr
1               5
```

<210> SEQ ID NO 8
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
aggacctggc ctggcggcgc cctcacagag cctgtccatc acatgcactg tctctgggtt      60
ctcattaacc agctatgtta taagttgggt tcgccagcca ccaggaaagg gtctggagtg     120
gcttggagta atatggactg gtggaggcac aaattataat tcagctctca aatccagact     180
gagcatcagc aaagacaact ccaagagtca agtttcctta aaaatgaaca gtctgcaaac     240
tgatgacaca gccaggtact actgtgccag cctttcctat gatggtttcg actactgggg     300
ccaagggacc acggtcac                                                   318

<210> SEQ ID NO 9
<211> LENGTH: 314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gacattctga tgacccagtc tccagcaatc atgtctgcat ctccagggga gaaggtcacc      60
atgaccrgca gtgccagmaa gtgtaagtta catgcactgg taccagcaga agtcaggcac     120
ctcccccaaa agatggattt atgacacatc camctggctt ctggagtccc tgctcgcttc     180
agtggcagtg ggtctgggac ctcttactct ctcamatcag cagcatggag gctgaagatg     240
ctgccactta ttactgccag cagtggagta gtaacccgct cacgttcggt gctgggacca     300
agctggaaat aaaa                                                       314

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Val Thr Tyr Asn Thr Asp Thr Phe Glu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Met Pro Asn Pro Glu Gly Arg Tyr Thr
1               5                   10

<210> SEQ ID NO 12
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 12

Tyr Asn Tyr Leu Ser Thr Asp Val Gly Ser
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Thr Leu Glu Glu Ile Thr Gly Tyr Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ile Ser Ala Trp Pro Asp Ser Leu Pro
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Ser Leu Thr Leu Gln Gly Leu Gly Ile
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Arg Glu Tyr Val Asn Ala Arg His Cys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Asp Gln Cys Val Ala Cys Ala His Tyr
1               5                   10
```

```
<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Ser Gly Val Lys Pro Asp Leu Ser Tyr
1               5                   10

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgaggtgcag ctggaggagt c                                              21

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgaccgtgg tcccttggcc ccag                                           24

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gacattctga tgacccagtc t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttttatttcc agcttggtcc c                                              21

<210> SEQ ID NO 23
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (2)..(319)
<220> FEATURE:
<221> NAME/KEY: modified_base
<222> LOCATION: (319)..(319)
<223> OTHER INFORMATION: a, c, t or g
```

<400> SEQUENCE: 23

```
a gga cct ggc ctg gcg gcg ccc tca cag agc ctg tcc atc aca tgc act      49
  Gly Pro Gly Leu Ala Ala Pro Ser Gln Ser Leu Ser Ile Thr Cys Thr
  1               5                   10                  15 gtc tct ggg ttc tca tta acc agc tat gtt ata agt tgg gtt cgc cag        97
Val Ser Gly Phe Ser Leu Thr Ser Tyr Val Ile Ser Trp Val Arg Gln
             20                  25                  30 cca cca gga aag ggt ctg gag tgg ctt gga gta ata tgg act ggt gga       145
Pro Pro Gly Lys Gly Leu Glu Trp Leu Gly Val Ile Trp Thr Gly Gly
         35                  40                  45 ggc aca aat tat aat tca gct ctc aaa tcc aga ctg agc atc agc aaa       193
Gly Thr Asn Tyr Asn Ser Ala Leu Lys Ser Arg Leu Ser Ile Ser Lys
     50                  55                  60 gac aac tcc aag agt caa gtt tcc tta aaa atg aac agt ctg caa act       241
Asp Asn Ser Lys Ser Gln Val Ser Leu Lys Met Asn Ser Leu Gln Thr
 65                  70                  75                  80 gat gac aca gcc agg tac tac tgt gcc agc ctt tcc tat gat ggt ttc       289
Asp Asp Thr Ala Arg Tyr Tyr Cys Ala Ser Leu Ser Tyr Asp Gly Phe
                 85                  90                  95 gac tac tgg ggc caa ggg acc acg gtc acn                               319
Asp Tyr Trp Gly Gln Gly Thr Thr Val Thr
            100                 105
```

<210> SEQ ID NO 24
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(288)

<400> SEQUENCE: 24

```
cag gtg cag ctg aag gag tca gga cct ggc ctg gtg gcg ccc tca cag        48
Gln Val Gln Leu Lys Glu Ser Gly Pro Gly Leu Val Ala Pro Ser Gln
1               5                   10                  15 agc ctg tcc atc aca tgc act gtc tct ggg ttc tca tta acc agc tat        96
Ser Leu Ser Ile Thr Cys Thr Val Ser Gly Phe Ser Leu Thr Ser Tyr
             20                  25                  30 gct ata agc tgg gtt cgc cag cca cca gga aag ggt ctg gag tgg ctt       144
Ala Ile Ser Trp Val Arg Gln Pro Pro Gly Lys Gly Leu Glu Trp Leu
         35                  40                  45 gga gta ata tgg act ggt gga ggc aca aat tat aat tca gct ctc aaa       192
Gly Val Ile Trp Thr Gly Gly Gly Thr Asn Tyr Asn Ser Ala Leu Lys
     50                  55                  60 tcc aga ctg agc atc agc aaa gac aac tcc aag agt caa gtt ttc tta       240
Ser Arg Leu Ser Ile Ser Lys Asp Asn Ser Lys Ser Gln Val Phe Leu
 65                  70                  75                  80 aaa atg aac agt ctg caa act gat gac aca gcc agg tac tac tgt gcc       288
Lys Met Asn Ser Leu Gln Thr Asp Asp Thr Ala Arg Tyr Tyr Cys Ala
                 85                  90                  95 ag                                                                    290
```

<210> SEQ ID NO 25
<211> LENGTH: 96
<212> TYPE: PRT
<213> ORGANISM: Artificial Sequence
<220> FEATURE:
<223> OTHER INFORMATION: Description of Artificial Sequence: Synthetic polypeptide -continued

```
<400> SEQUENCE: 25

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Ala Ile Ser Trp Val Arg Gln Pro Pro Gly Lys Gly Leu Glu Trp Leu
        35                  40                  45

Gly Val Ile Trp Thr Gly Gly Thr Asn Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

<210> SEQ ID NO 26
<211> LENGTH: 266
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
aggacctggc ctggtggcgc cctcacagag cctgtccatt acctgcactg tctctgggtt      60
ctcattaacc agctatgata taagctggat tcgccagcca ccaggaaagg gtctggagtg    120
gcttggagta atatggactg gtggaggcac aaattataat tcagctttca tgtccagact    180
gagcatcagc aaggacaact ccaagagcca agttttctta aaaatgaaca gtctgcaaac    240
tgatgacaca gccatatatt actgtg                                         266

<210> SEQ ID NO 27
<211> LENGTH: 270
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
aggacctggc ctggtggcgc cctcacagag cctgtccatc acatgcactg tctctgggtt      60
ctcattaacc agctatggtg tagactgggt tcgccagtct ccaggaaagg gtctggagtg    120
gctgggagta atatggggtg ttggaagcac aaattataat tcagctctca aatccagact    180
gagcatcagc aaggacaact ccaagagcca agttttctta aaaatgaaca gtctgcaaac    240
tgatgacaca gccatgtact actgtgccag                                     270

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctatgatggt tactac                                                     16

<210> SEQ ID NO 29
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
cctactatgg ttacgac                                                    17

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctactatggt tacgac                                                     16

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tttgactact ggggccaagg caccactctc ac                                   32

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
atgctatgga ctactggggt caaggaacct cagtcac                              37

<210> SEQ ID NO 33
<211> LENGTH: 270
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
aggacctggc ctggtggcgc cctcacagag cctgtccatc acttgcactg tctctgggtt     60
ttcattaacc agctatggtg tacactgggt tcgccagcct ccaggaaagg gtctggagtg    120
gctgggagta atatgggctg gtggaagcac aaattataat tcggctctca tgtccagact    180
gagcatcagc aaagacaact ccaagagcca agttttctta aaaatgaaca gtctgcaaac    240
tgatgacaca gccatgtact actgtgccag                                    270

<210> SEQ ID NO 34
<211> LENGTH: 270
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
aggacctggc ctggtggcgc cctcacagag cctgtccatc acttgcactg tctctgggtt     60
```

```
ttcattaacc agctatggtg tacactgggt tcgccagcct ccaggaaagg gtctggagtg      120
gctgggagta atatgggctg gtggaagcac aaattataat tcggctctca tgtccagact      180
gagcatcagc aaagacaact ccaagagcca agttttctta aaaatgaaca gtctgcaaac      240
tgatgacaca gccatgtact actgtgccag                                      270
```

<210> SEQ ID NO 35
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
aggacctggc ctggtggcgc cctcacagag cctgtccatc acttgcactg tctctgggtt      60
ttcattaacc agctatggtg tagactgggt tcgccagcct ccaggaaagg gtctggagtg     120
gctgggagta atatggggtg gtggaagcac aaattataat tcagctctca tgtccagact     180
gagcatcagc aaagacaact ccaagagcca agttttctta aaaatgaaca gtctgcaaac     240
tgatgacaca gccatgtact actgtgcca                                      269
```

<210> SEQ ID NO 36
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
aggacctggc ctggtggcgc cctcacagag cctgtccatc acatgcactg tctcagggtt      60
ctcattaacc gactatggtg taagctggat tcgccagcct ccaggaaagg gtctggagtg     120
gctgggagta atatggggtg gtggaagcac atactataat tcagctctca aatccagact     180
gagcatcagc aaggacaact ccaagagcca agttttctta aaaatgaaca gtctgcaaac     240
tgatgacaca gccatgtact actgtgcca                                      269
```

<210> SEQ ID NO 37
<211> LENGTH: 270
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
aggacctggc ctggtggcgc cctcacagag cctgtccatc acatgcaccg tctcagggtt      60
ctcattaacc ggctatggtg taaactgggt tcgccagcct ccaggaaagg gtctggagtg     120
gctgggaatg atatggggtg atggaagcac agactataat tcagctctca aatccagact     180
gagcatcagc aaggacaact ccaagagcca agttttctta aaaatgaaca gtctgcaaac     240
tgatgacaca gccaggtact actgtgccag                                      270
```

<210> SEQ ID NO 38
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
aggacctggc ctggtggcgc cctcacagag cctgtccatc acatgcactg tctcagggtt      60
ctcattaacc agctatggtg taagctgggt tcgccagcct ccaggaaagg gtctggagtg     120
gctgggagta atatggggtg acgggagcac aaattatcat tcagctctca tatccagact     180
gagcatcagc aaggataact ccaagagcca agttttctta aaactgaaca gtctgcaaac     240
tgatgacaca gccacgtact actgtgcca                                        269
```

<210> SEQ ID NO 39
<211> LENGTH: 269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
aggacctggc ctggtggcgc cctcacagag cctgtccatc acatgcactg tctcagggtt      60
ctcattaacc agctatggtg taagctgggt tcgccagcct ccaggaaagg gtctggagtg     120
gctgggagta atatggggtg acgggagcac aaattatcat tcagctctca tatccagact     180
gagcatcagc aaggataact ccaagagcca agttttctta aaactgaaca gtctgcaaac     240
tgatgacaca gccacgtact actgtgcca                                        269
```

<210> SEQ ID NO 40
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(315)

<400> SEQUENCE: 40

```
att ctg atg acc cag tct cca gca atc atg tct gca tct cca ggg gag        48
Ile Leu Met Thr Gln Ser Pro Ala Ile Met Ser Ala Ser Pro Gly Glu
1               5                   10                  15 aag gtc acc atg acc tgc agt gcc agc tca agt gta agt tac atg cac        96
Lys Val Thr Met Thr Cys Ser Ala Ser Ser Ser Val Ser Tyr Met His
            20                  25                  30 tgg tac cag cag aag tca ggc acc tcc ccc aaa aga tgg att tat gac       144
Trp Tyr Gln Gln Lys Ser Gly Thr Ser Pro Lys Arg Trp Ile Tyr Asp
        35                  40                  45 aca tcc aaa ctg gct tct gga gtc cct gct cgc ttc agt ggc agt ggg       192
Thr Ser Lys Leu Ala Ser Gly Val Pro Ala Arg Phe Ser Gly Ser Gly
    50                  55                  60 tct ggg acc tct tac tct ctc aca atc agc agc atg gag gct gaa gat       240
Ser Gly Thr Ser Tyr Ser Leu Thr Ile Ser Ser Met Glu Ala Glu Asp
65                  70                  75                  80 gct gcc act tat tac tgc cag cag tgg agt agt aac ccg ctc acg ttc       288
Ala Ala Thr Tyr Tyr Cys Gln Gln Trp Ser Ser Asn Pro Leu Thr Phe
                85                  90                  95 ggt gct ggg acc aag ctg gaa ata aaa                                    315
Gly Ala Gly Thr Lys Leu Glu Ile Lys
            100                 105
```

<210> SEQ ID NO 41
<211> LENGTH: 282
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(282)
<220> FEATURE:
<221> NAME/KEY: modified_base
<222> LOCATION: (282)..(282)
<223> OTHER INFORMATION: a, c, t or g

<400> SEQUENCE: 41

```
caa att gtt ctc acc cag tct cca gca atc atg tct gca tct cca ggg        48
Gln Ile Val Leu Thr Gln Ser Pro Ala Ile Met Ser Ala Ser Pro Gly
1               5                   10                  15 gag aag gtc acc atg acc tgc agt gcc agc tca agt gta agt tac atg        96
Glu Lys Val Thr Met Thr Cys Ser Ala Ser Ser Val Ser Tyr Met
            20                  25                  30 cac tgg tac cag cag aag tca ggc acc tcc ccc aaa aga tgg att tat       144
His Trp Tyr Gln Gln Lys Ser Gly Thr Ser Pro Lys Arg Trp Ile Tyr
        35                  40                  45 gac aca tcc aaa ctg gct tct gga gtc cct gct cgc ttc agt ggc agt       192
Asp Thr Ser Lys Leu Ala Ser Gly Val Pro Ala Arg Phe Ser Gly Ser
    50                  55                  60 ggg tct ggg acc tct tac tct ctc aca atc agc agc atg gag gct gaa       240
Gly Ser Gly Thr Ser Tyr Ser Leu Thr Ile Ser Ser Met Glu Ala Glu
65                  70                  75                  80 gat gct gcc act tat tac tgc cag cag tgg agt agt aac ccn               282
Asp Ala Ala Thr Tyr Tyr Cys Gln Gln Trp Ser Ser Asn Pro
                85                  90
```

<210> SEQ ID NO 42
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro
                85                  90
```

<210> SEQ ID NO 43
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
attgttctca cccagtctcc agcaatcatg tctgcatctc caggggagaa ggtcaccatg        60
```

```
acctgcagtg ccagctcaag tataagttac atgcactggt accagcagaa gccaggcacc    120 tccccccaaaa gatggattta tgacacatcc aaactggctt ctggagtccc tgctcgcttc    180
agtggcagtg gtctgggac ctcttattct ctcacaatca gcagcatgga ggctgaagat    240
gctgccactt attactgcca tcagcggagt agttaccc                             278
```

```
<210> SEQ ID NO 44
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
attgttctca cccagtctcc agcactcatg tctgcatctc caggggagaa ggtcaccatg      60
acctgcagtg ccagctcaag tgtaagttac atgtactggt accagcagaa gccaagatcc    120 tccccccaaac cctggattta tctcacatcc aacctggctt ctggagtccc tgctcgcttc    180
agtggcagtg gtctgggac ctcttactct ctcacaatca gcagcatgga ggctgaagat    240
gctgccactt attactgcca gcagtggagt agtaaccc                             278
```

```
<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctcacgttcg gtgctgggac caagctggag ctgaaa                               36
```

```
<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cacgttcgga gggggacca agctggaaat aaaa                                  34
```

```
<210> SEQ ID NO 47
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
attcttctca cccagtctcc agcaatcatg tctgcatctc caggggagaa ggtcaccatg      60
acctgcagtg ccagctcaag tgtaagttac atgcactggt accagcagaa gccaggatcc    120
tcgcccaaac cctggattta tgacacatcc aacctggctt ctggattccc tgctcgcttc    180
agtggcagtg gtctgggac ctcttactct ctcataatca gcagcatgga ggctgaagat    240
gctgccactt attactgcca tcagcggagt agttaccc                             278
```

```
<210> SEQ ID NO 48
<211> LENGTH: 278
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 48
attgttctca cccagtctcc agcaatcatg tctgcatctc caggggagaa ggtcaccatg    60
acctgcagtg ccagctcaag tgtaagttac atgcactggt accagcagaa gccaggatcc   120
tcccccagac tctggattta tttaacattc aacttggctt ctggagtccc tgctcgcttc   180
agtggcagtg gtctgggac ctcttactct ctctcaatca gcagcatgga ggctgaagat    240
gctgccactt attactgcca gcagtggagt agtaaccc                            278

<210> SEQ ID NO 49
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
attgttctca cccagtctcc agcaatcatg tctgcatctc caggggagaa ggtcaccatg    60
acctgcagtg ccagctcaag tgtaagttac atgtactggt accagcagaa gccaggatcc   120
tcccccagac tcctgattta tgacacatcc aacctggctt ctggagtccc tgttcgcttc   180
agtggcagtg gtctgggac ctcttactct ctcacaatca gccgaatgga ggctgaagat    240
gctgccactt attactgcca gcagtggagt agttaccc                            278

<210> SEQ ID NO 50
<211> LENGTH: 268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
cccagtctcc agcaatcctg tctgcatctc caggggagaa ggtcacaatg acttgcaggg    60
ccagctcaag tgtaagttac atgcactggt accagcagaa gccaggatcc tcccccaaac   120
cctggattta tgccacatcc aacctggctt ctggagtccc tgctcgcttc agtggcagtg   180
ggtctgggac ctcttactct ctcacaatca gcagagtgga ggctgaagat gctgccactt   240
attactgcca gcagtggagt agtaaccc                                      268

<210> SEQ ID NO 51
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
attgttctca cccagtctcc agcaatcatg tctgcatctc caggggaaaa ggtcaccatg    60
acctgcagtg ccagctcaag tgtaagttac atgtactggt accagcagaa gccaggctcc   120
tcccccagac tctggattta tgacacatcc aacctggttt ctggagtccc tgctcgcttc   180
agtggcagta ggtctgggac ctcttattct ctcacaatca gcagcatgga ggctgaagat   240
gctgccactt attactgcca gcagtacagt ggttaccc                            278

```
<210> SEQ ID NO 52
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
attgttctca cccagtctcc agcaatcatg tctgcatctc caggggagaa ggtcaccata        60
acctgcagtg ccagctcaag tgtaagttac atgcactggt tccagcagaa gccaggcact       120
tctcccaaac tctggattta tagcacatcc aacctggctt ctggagtccc tgctcgcttc       180
agtggcagtg gatctgggac ctcttactct ctcacaatca gccgaatgga ggctgaagat       240
gctgccactt attactgcca gcaaaggagt agttaccc                               278

<210> SEQ ID NO 53
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
attgttctca cccagtctcc agcaatcatg tctgcatctc caggggagaa ggtcaccata        60
tcctgcagtg ccagctcaag tgtaagttac atgtactggt accagcagaa gccaggatcc       120
tcccccaaac cctggattta tcgcacatcc aacctggctt ctggagtccc tgctcgcttc       180
agtggcagtg gtctgggac ctcttactct ctcacaatca gcagcatgga ggctgaagat        240
gctgccactt attactgcca gcagtatcat agttaccc                               278
```

MONOCLONAL ANTIBODIES AGAINST HER2 ANTIGENS, AND USES THEREFOR

CROSS-REFERENCE TO RELATED APPLICATIONS

The present application is a divisional of U.S. patent application Ser. No. 13/087,351, now U.S. Pat. No. 8,349,585 B2, filed on Apr. 14, 2011, which claims the benefit of U.S. Provisional Application No. 61/324,490, filed on Apr. 15, 2010, the contents of all of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 27, 2013, is named 12112.0001-01000_SL.txt and is 28,187 bytes in size.

FIELD OF THE DISCLOSURE

The present disclosure generally relates to monoclonal antibodies (mAbs), hybridoma lines that secrete antibodies or fragments thereof, and the use of antibodies and antibody fragments to preferentially detect antigens.

BACKGROUND

The Her2/neu (ErbB2) gene encodes a 185 kDa transmembrane glycoprotein that belongs to the family of epidermal growth factor receptors. It consists of a 620 aa extracellular domain, followed by a 23 aa transmembrane domain and a 490 aa intracellular domain with a tyrosine kinase activity. Akiyama T, et al., *Science* 1986, 232(4758):1644-1646. These results suggest that ECD/Her2 is a good candidate for a tumor antigen vaccine as it prolongs tumor free survival and overall survival of vaccinated mice.

HER2 antibodies with various properties have been described in Tagliabue et al., *Int. J. Cancer* 47:933-937 (1991); McKenzie et al., *Oncogene* 4:543-548 (1989); Maier et al., *Cancer Res.* 51:5361-5369 (1991); Bacus et al., *Molecular Carcinogenesis* 3:350-362 (1990); Stancovski et al., *PNAS (USA)* 88:8691-8695 (1991); Bacus et al., *Cancer Research* 52:2580-2589 (1992); Xu et al., *Int. J. Cancer* 53:401-408 (1993); WO94/00136; Kasprzyk et al., *Cancer Research* 52:2771-2776 (1992); Hancock et al., *Cancer Res.* 51:4575-4580 (1991); Shawver et al., *Cancer Res.* 54:1367-1373 (1994); Arteaga et al., *Cancer Res.* 54:3758-3765 (1994); Harwerth et al., *J. Biol. Chem.* 267:15160-15167 (1992); U.S. Pat. No. 5,783,186; Kao et al., U.S. Publ. No. 2009/0285837 (2009); Ross et al., *The Oncologist* 8:307-325 (2003) and Klapper et al., *Oncogene* 14:2099-2109 (1997), each of which is incorporated herein by reference in its entirety.

The trastuzumab antibody (monoclonal antibody therapy huMAb4D5-8, rhuMAb HER2, trastuzumab, commercially available as Herceptin® (U.S. Pat. No. 5,821,337, herein incorporated by reference in its entirety)) has been the subject of HER-2 research assays. See Sapino, A., et al., *Annals of Oncology* (2007) 18: 1963-1968; Bussolati, G, et al., *British Journal of Cancer* (2005) 92, 1261-1267; and Glazyrin A, et al., *J Histology & Cytochemistry* (2007) 55(1):25-33. Trastuzumab recognizes the extracellular domain of HER-2, but requires modification, for example by biotinylation, to be used in immunocytochemistry and other non-therapy applications. The immunoreactivity of biotinylated trastuzumab, however, is lost after 3 months so that a diagnostic assay with trastuzumab as the primary antibody would never be commercially viable. Moreover, a biotinylated trastuzumab does not recognize a native secretory form of the HER-2 antigen in blood samples in an ELISA assay. Trastuzumab has been shown to be more accurate than the commercially available HER-2 antibodies used for diagnostic uses such as immunohistochemistry, in identifying a subset of HER2-amplified breast cancer patients who are more likely to most benefit from trastuzumab-based treatments. Id.

Accordingly, there is a need for other HER-2 monoclonal antibodies that are more accurate in determining a proper patient population for therapy than the currently commercially available HER-2 antibodies. Moreover, there is a need that such more accurate HER-2 monoclonal antibodies do not require modification, such as with biotinylation, so that they have the confirmed long-term stability necessary for commercial viability in a diagnostic assay. Also HER-2 monoclonal antibodies that recognize a native secretory form of HER-2 protein with high specificity and sensitivity in blood samples for blood and ELISA assays, as well as immunocytochemistry, are needed.

SUMMARY OF THE INVENTION

The present invention provides an antibody capable of preferentially binding to a soluble form of HER2 with a specific affinity of between $10^{-8}$M and $10^{-11}$M.

The present invention also provides an antibody capable of binding to a soluble form of HER2.

The present invention also provides an antibody capable of selectively reducing the activity of a soluble HER2.

The present invention also provides an antibody capable of preferentially binding to a soluble form of a HER2 antigen.

The present invention also provides an antibody capable of preferentially binding to a soluble form of a HER2 antigen, where the preferential binding is relative to a membrane form of HER2.

The present invention also provides a method of determining the status of a cell in a sample by (a) obtaining said sample; (b) contacting said sample with an antibody capable of preferentially detecting a soluble form of HER2 antigen; and (c) determining quantity or localization of said antigen.

The present invention also provides an antibody specific for a HER2 antigen, comprising the heavy chain CDR antigen binding site sequences CDR1, CDR2, and CDR3 as set forth in FIG. 2, and the light chain CDR antigen binding site sequences CDR1, CDR2, and CDR3 as set forth in FIG. 3.

The present invention also provides an antibody specific for a HER2 antigen, comprising one or more of the heavy chain CDR antigen binding site sequences set forth in FIG. 2, and one or more of the light chain CDR antigen binding site sequences set forth in FIG. 3.

The present invention also provides an isolated DNA sequence which encodes the heavy chain of an antibody molecule, where the antibody molecule has specificity for HER2 and where the variable domain of said heavy chain comprises a CDR having the antigen binding site sequences CDR1, CDR2, and CDR3 set forth in FIG. 2.

The present invention also provides an isolated DNA sequence which encodes the light chain of an antibody molecule, where the antibody molecule has specificity for HER2 and further where the variable domain of the light chain comprises a CDR having the antigen binding site sequences CDR1, CDR2, and CDR3 set forth in FIG. 3.

The present invention also provides a composition comprising a tissue specimen, an antibody-antigen complex between an antibody capable of preferentially binding to a soluble form of HER2 antigen and a soluble form of HER2 antigen within said tissue specimen, preferably, said tissue specimen is from a patient suffering from breast cancer.

The present invention also provides an immunoassay for detecting a HER2 antigen which binds to a monoclonal antibody having one or more of the heavy chain CDR antigen binding site sequences set forth in FIG. 2, and one or more of the light chain CDR antigen binding site sequences set forth in FIG. 3, comprising: (a) contacting the sample with an effective binding amount of the antibody according to claim 1 or claim 2; and (b) detecting the antigen by detecting the binding of the antibody to the HER2 antigen.

The present invention also provides a method for developing drugs useful in treating and/or diagnosing diseases characterized by the expression of gene products of HER2 and homologues thereof, comprising the steps of: identifying gene products expressed by HER2 and homologues thereof in a subject having a disease, and utilizing the gene products as biomarkers in the development and identification of drugs selected from the group consisting of HER2 antibodies and antibody fragments, inhibiting peptides, siRNA, antisense oligonucleotides, vaccines, and chemical compounds, which specifically target the gene products.

The present invention also provides a method of determining the status of a cell in a sample comprising: (a) obtaining the sample from a patient; (b) contacting the sample with an antibody capable of preferentially detecting a soluble form of HER2 antigen; and (c) determining the quantity of the antigen.

The present invention also provides a method of determining the status of a cell in a sample comprising: (a) obtaining the sample from a patient; (b) contacting the sample with an antibody capable of preferentially detecting a soluble form of HER2 antigen; and (c) determining the localization of the antigen.

The present invention also provides an antibody capable of preferentially binding to a secreted form of HER2 antigen.

The present invention also provides a method of determining the status of a cell in a sample comprising: (a) obtaining the sample from a patient; (b) contacting the sample with an antibody capable of preferentially detecting a secreted form of HER2 antigen; and (c) determining the quantity of the antigen.

The present invention also provides a method of determining the status of a cell in a sample comprising: (a) obtaining the sample from a patient; (b) contacting the sample with an antibody capable of preferentially detecting a secreted form of HER2 antigen; and (c) determining the localization of the antigen.

The present invention also provides an antibody capable of preferentially binding to a secreted form of HER2 with a specific affinity of between $10^{-8}$M and $10^{-11}$M.

The present invention also provides an antibody capable of binding a secreted form of HER2.

The present invention also provides an antibody capable of selectively reducing the activity of a secreted HER2.

The present invention also provides a method of determining the status of a cell in a sample comprising: (a) obtaining the sample; (b) contacting the sample with an antibody capable of preferentially detecting a secreted form of HER2 antigen; and (c) determining the quantity or localization of the antigen.

The present invention also provides a method of detecting breast cancer in a tissue specimen comprising: (a) obtaining the tissue specimen, (b) contacting the tissue specimen with an antibody capable of preferentially binding a soluble form of HER2 antigen, (c) staining said tissue specimen with an immunohistochemical staining, and wherein said staining indicates presence of breast cancer in said tissue specimen.

The present invention also provides a use of a composition comprising a tissue specimen, an antibody-antigen complex between an antibody capable of preferentially binding to a soluble form of HER2 antigen and a soluble form of HER2 antigen within said tissue specimen, for detecting breast cancer comprising: immunohistochemical staining of said composition wherein said staining indicates the presence of breast cancer.

The present invention also provides an antibody that is preferably an antibody capable of preferentially binding to a soluble form of HER2 antigen. Most preferably, said antibody is Alper-HER2 mAb 2HE antibody. In one aspect of the invention, the antibody can be used to detect the presence of HER2 in a breast tissue.

BRIEF DESCRIPTION OF THE DRAWINGS

FIGS. 2A-E. Alper-HER2 mAb 2HE heavy chain sequence information. FWRs and CDRs of the heavy chain of a Alper-HER2 mAb (2HE), in which the polypeptide sequence provided in the top line corresponds to the sequence of the Alper-HER2 mAb (2HE). Amino acid residues are numbered using the convention of Kabat et al., (1991) Sequences of Proteins of Immunological Interest, $5^{th}$ Edition, Department of Health and Human Services, Public Health Service, National Institutes of Health, Bethesda (NIH Publication No. 91-3242). Bold residues set forth in underlined text indicate specificity determining residues (SDRs). FIGS. 2A, 2B, 2C, 2D, and 2E disclose SEQ ID NOS 1, 23, 25, 24, and 26-39, respectively, top to bottom, in order of appearance.

FIGS. 3A-E. Alper-HER2 mAb (2HE) light chain sequence information. FWRs and CDRs of the light chain of a Alper-HER2 mAb (2HE), in which the polypeptide sequence provided in the top line corresponds to the sequence of the Alper-HER2 mAb (2HE). Amino acid residues are numbered using the convention of Kabat et al. Bold residues set forth in underlined text indicate the specificity determining residues (SDRs). FIGS. 3A, 3B, 3C, 3D, and 3E disclose SEQ ID NOS 5, 40, 42, 41, and 43-53, respectively, top to bottom, in order of appearance.

BRIEF DESCRIPTION OF THE SEQUENCES

Figure 1:
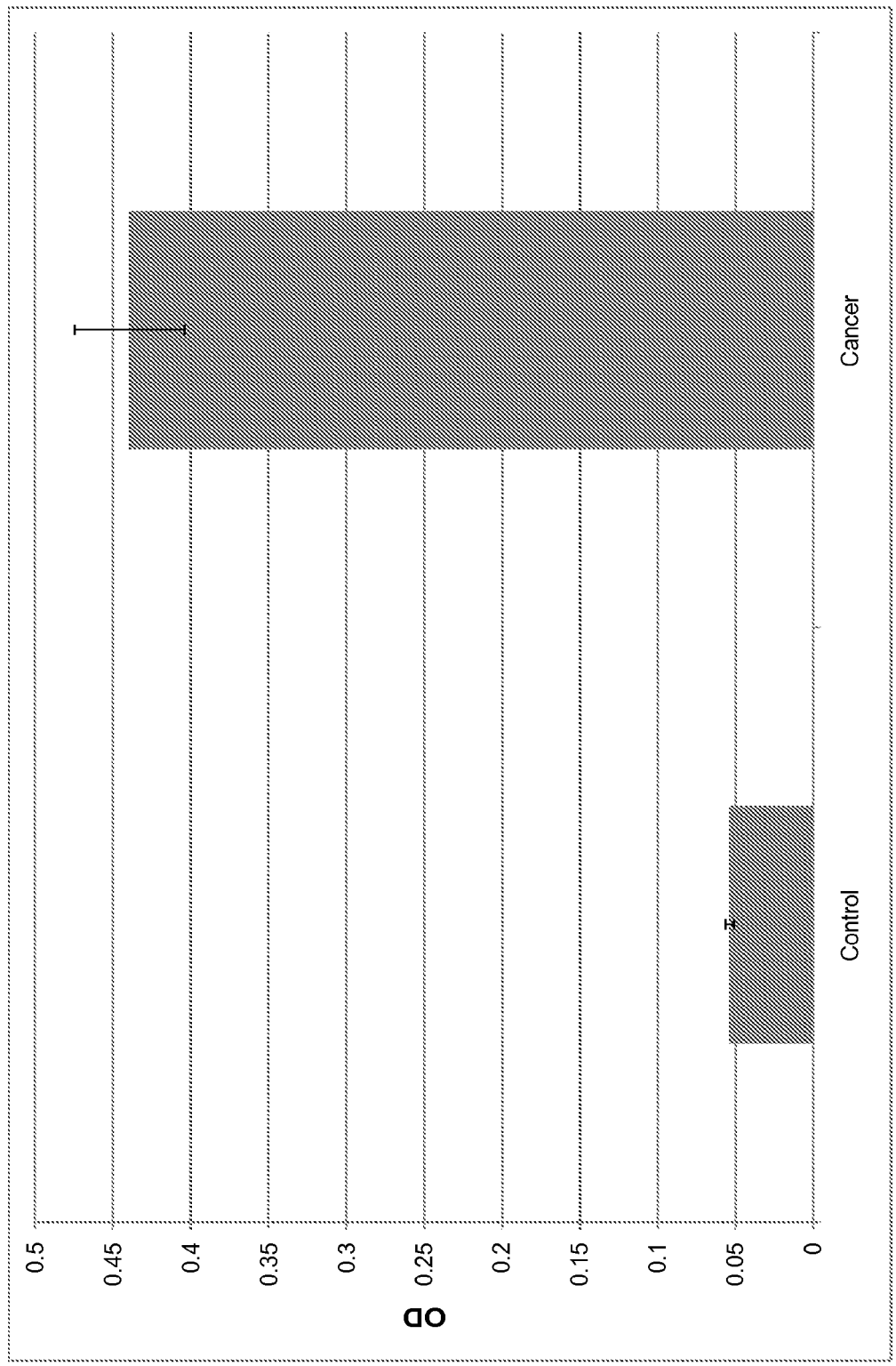
FIG. 1. Clinical significance of HER2 plasma levels in control group (n=5) and breast cancer patient (non-metastatic and metastatic) group (n=15) sera, determined by competitive ELISA with Alper-HER2 mAb 2HE.

SEQ ID NO: 1 shows the amino acid sequence of Alper-HER2 mAb (2HE) Heavy Chain

SEQ ID NO: 2 shows CDR1 of Alper-HER2 mAb (2HE) Heavy Chain

SEQ ID NO: 3 shows CDR2 of Alper-HER2 mAb (2HE) Heavy Chain

SEQ ID NO: 4 shows CDR3 of Alper-HER2 mAb (2HE) Heavy Chain

SEQ ID NO: 5 shows the amino acid sequence of Alper-HER2 mAb (2HE) Kappa Chain

SEQ ID NO: 6 shows CDR1 of Alper-HER2 mAb (2HE) Kappa Chain

SEQ ID NO: 7 shows CDR3 of Alper-HER2 mAb (2HE) Kappa Chain

SEQ ID NO: 8 shows the nucleotide sequence of Alper-HER2 mAb (2HE) Heavy Chain

SEQ ID NO: 9 shows the nucleotide sequence of Alper-HER2 mAb (2HE) Kappa Chain

SEQ ID NO: 10 shows the amino acid sequence of Epitope 1 of HER2

SEQ ID NO: 11 shows the amino acid sequence of Epitope 2 of HER2

SEQ ID NO: 12 shows the amino acid sequence of Epitope 3 of HER2

SEQ ID NO: 13 shows the amino acid sequence of Epitope 4 of HER2

SEQ ID NO: 14 shows the amino acid sequence of Epitope 5 of HER2

SEQ ID NO: 15 shows the amino acid sequence of Epitope 6 of HER2

SEQ ID NO: 16 shows the amino acid sequence of Epitope 7 of HER2

SEQ ID NO: 17 shows the amino acid sequence of Epitope 8 of HER2

SEQ ID NO: 18 shows the amino acid sequence of Epitope 9 of HER2

DETAILED DESCRIPTION

1. Definitions

Antibody: This refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody of the present invention having specificity toward a desired target epitope or epitopes. In an aspect, an antibody of the present invention is Alper-HER2 mAb 2HE. In another aspect, an antibody of the present invention includes one or more of the heavy chain CDR antigen binding site sequences CDR1, CDR2 and CDR3 as set forth in FIG. 2, and one or more of the light chain CDR antigen binding site sequences CDR1, CDR2 and CDR3 as set forth in FIG. 3.

Monoclonal Antibody: This refers to antibodies that are identical because they are produced by one type of immune cell that are all clones of a single parent cell. The monoclonal antibodies of the present invention can include intact monoclonal antibodies, antibody fragments, conjugates, or fusion proteins, which contain a $V_H$ and a $V_L$ where the CDRs form the antigen binding site.

Chimeric Antibody: This refers to an antibody which includes sequences derived from two different antibodies, which typically are of different species. Most typically, chimeric antibodies include human and non-human antibody fragments, generally human constant and non-human variable regions. Humanized antibodies can or can not be considered chimeric.

Humanized Antibody: This refers to an antibody derived from a non-human antibody. The humanized antibody retains or substantially retains the antigen-binding properties of the parent antibody but is less immunogenic in humans than its parent antibody.

Antibody Conjugates, Fusion Proteins, and Bispecific Antibodies: These refer to monoclonal antibodies conjugated by chemical methods with radionuclides, drugs, macromolecules, or other agents.

Antigen: This refers to one or more molecules or one or more portions of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly preferential manner, with its corresponding antibody and not with the multitude of other antibodies which can be evoked by other antigens. The binding of antigen to antibody must be above background levels.

Epitope: This refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes recognizing a phosphorylated native conformation of a HER2 extracellular domain. Such epitope can be any of SEQ ID NOs: 10-18. An Alper HER2 mAB 2HE epitope can be identified with a cross-clocking assay such as described in Antibodies, A Laboratory Manual, Cold Spring Harbor Laboratory, Ed Harlow and David Lane (1988), herein incorporated by reference in its entirety.

Complementarity Determining Region, or CDR: This refers to amino acid sequences which together define the binding affinity and specificity of the natural Fv region of a native immunoglobulin binding site. The light and heavy chains of an immunoglobulin each have three CDRs. By definition, the CDRs of the light chain are bounded by the residues at positions 26 and 30 (CDR1), 48 and 50 (CDR2), 87 and 92 (CDR3); the CDRs of the heavy chain are bounded by the residues at positions 19 and 26 (CDR1), 44-50 (CDR2), and 89-99 (CDR3), using the numbering convention delineated by Kabat et al., (1991) Sequences of Proteins of Immunological Interest, 5th Edition, Department of Health and Human Services, Public Health Service, National Institutes of Health, Bethesda (NIH Publication No. 91-3242), herein incorporated by reference in its entirety.

Framework Region or FWR: This refers to amino acid sequences interposed between CDRs. These portions of the antibody serve to hold the CDRs in an appropriate orientation for antigen binding.

Specificity Determining Residue, or SDR: This refers to amino acid residues unique to Alper-HER2 mAb (2HE) when compared to other IgGs. Preferentially, the SDR is the part of an immunoglobulin that is directly involved in antigen contact.

Constant Region: This refers to the portion of an antibody molecule which confers effector functions. A heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. A light chain constant region can be of the kappa or lambda type, preferably the kappa type.

Immunogenicity: A measure of the ability of a targeting protein or therapeutic moiety to elicit an immune response (humoral or cellular) when administered to a recipient. The present invention is concerned with the immunogenicity of antibodies to HER2.

Immunoreactivity: A measure of the ability of an immunoglobulin to recognize and bind to a specific antigen.

HER2 Antibodies or HER2 mAbs: This refers to antibodies preferential to expression products of the HER2 gene and homologues of the HER2 gene, which can include antibodies specific to modified forms of the expression product that are produced by cancer cells. The antibodies include variants, such as chimeric, humanized, and other variants known to those skilled in the art. HER2 antibodies are said to be specific for the HER2 antigen or epitope of the present invention if they exhibit preferential binding to a HER2 antigen or epitope with a binding affinity at least 10 fold, at least 50 fold, at least 100 fold or at least 500 fold higher relative to another protein. In an aspect, HER2 antibodies are said to be specific for the HER2 antigen or epitope of the present invention if they bind with greater than 1000 fold higher affinity relative to any other protein. In an aspect, a HER2 antibody of the present invention is Alper-HER2 mAb 2HE. In another aspect, a HER2 antibody of the present invention includes one or more of the heavy chain CDR antigen binding site sequences CDR1, CDR2 and CDR3 as set forth in FIG. 2, and one or more of the light chain CDR antigen binding site sequences CDR1, CDR2 and CDR3 as set forth in FIG. 3. A naked HER2 antibody is a HER2 antibody of the present invention that is not conjugated or otherwise bound to a heterologous molecule, such as biotin or radiolabel.

HER2 Antigens: This refers to expression products generated by HER2, which can be used as antigens, target molecules, biomarkers, or any combination thereof. A HER2 antigen can be produced by the HER2 gene and homologues of the HER2 gene, and can include various modifications introduced by the cells expressing a HER2 antigen, such as cancer cells. In an aspect, a modification is tyrosine phosphorylation.

Substantially Similar Binding Properties: This refers to a chimeric antibody, such as a humanized antibody or fragments thereof which retain the ability to preferentially bind an antigen recognized by the parent antibody used to produce the chimeric antibody, such as a humanized antibody, or fragments thereof. Preferably, the affinity of a chimeric antibody, humanized antibody, or antibody fragment is at least about 10% of the affinity of the parent antibody, more preferably at least about 25%, even more preferably at least about 50%. Most preferably, a chimeric antibody, preferably a humanized antibody, or antibody fragments thereof exhibit an antigen-binding affinity that is at least about 75% of the affinity of the parent antibody. Methods for assaying antigen-binding affinity are known in the art and include half-maximal binding assays, competition assays, and Scatchard analysis. In a preferred aspect, antigen-binding affinity is assayed using a competition assay.

Substantially Homologous: Refers to immunoglobulin sequences that exhibit at least about 85% identity, more preferably about 90% identity, most preferably about 95% identity with a reference immunoglobulin sequence, where percent identity is determined by comparing the number identical of amino acid residues between the two immunoglobulins, where the positions of the amino acid residues are indicated, such as by using the Kabat numbering scheme.

Sameness for Monoclonal Antibody Products: For the purpose of determining sameness of monoclonal antibodies, and products thereof, the complementarity determining regions of the heavy and light chain variable regions are the principal molecular structural feature of a monoclonal antibody product. Two monoclonal antibodies can be considered the same if the amino acid sequences of the CDRs were the same, or if there were only minor amino acid differences between them. Whether differences in the amino acid sequences are minor can be determined by factors that include (but are not limited to) whether any particular residues have been established to be important for antigen binding, such as to be a Specificity Determining Residue. Amino acid differences outside the CDRs, or differences due to glycosylation patterns or post translational modifications do not result in different monoclonal antibodies. Changes in antibody structure that do not constitute differences between two monoclonal antibody products with the same CDRs include changes in the FWRs (i.e., humanizing a non-human derived monoclonal antibody or engineering certain framework residues that are important for antigen contact or for stabilizing the binding site, or changes in the constant region (i.e., changing the class or subclass of the constant region, changing specific amino acid residues which might alter an effector function, or changing the species from which the constant region is derived).

Substantially pure: For the purpose of the present invention, substantially pure refers to a homogeneous preparation preferably of a HER2 antibody or antibody fragment, or other chemical or biological agents. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

HER2 antigen expression: includes measurement of presence or abundance of HER2 antigen in a particular tissue specimen, blood, serum, or plasma, preferably, a tissue specimen from a patient suffering from a disease characterized by the expression of gene products of HER2 and homologues thereof, such diseases include breast cancer, stomach cancer, and colon cancer. In an aspect, breast cancer is characterized by HER2 overexpression and patients with a disease likely to improve from treatment with trastuzumab can be characterized by HER2 antigen expression with an epitope of the present invention.

2. Antibodies and Antibody Fragments

The present invention includes antibodies and antibody fragments preferential for HER2 antigens, including an antibody or antibody fragment capable of binding to a soluble form of HER2 (sHER2) with a specific affinity of between $10^{-8}$ M and $10^{-11}$ M; an antibody or antibody fragment capable of binding to a soluble form of HER2; an antibody or antibody fragment capable of selectively reducing the activity of a soluble HER2; and an antibody or antibody fragment capable of preferentially binding to a HER2.

An antibody or antibody fragment can be any antibody or antibody fragment and, without limitation, can be a monoclonal antibody, a chimeric antibody, a humanized antibody, or an antibody conjugate. In an aspect, an antibody is a mouse monoclonal antibody that identifies a human HER2 antigen of the present invention.

In an aspect, an antibody or antibody fragment can be any gamma globulin protein found in blood or other bodily fluids of vertebrates, and used by the host immune system to identify and neutralize foreign objects, such as bacteria and viruses. In one aspect, the antibody or antibody fragment can be selected from an antibody, a monoclonal antibody, a chimeric antibody, a humanized antibody, or an antibody conjugate. In an aspect, an antibody or antibody fragment can be any type of immunoglobulin protein, such as IgA, IgD, IgE, IgG or IgM. In an aspect, an antibody can be an IgG.

In one aspect, an antibody or antibody fragment is capable of reducing the activity of HER2 in at least one form, including a soluble form. In another aspect, an antibody or antibody fragment is capable of reducing the activity of HER2 in a secreted form. HER2 activity is determined by measuring the poly(rC) binding of a sample. In an aspect, the poly(rC)-binding assay is carried out using a gel-shift assay as described in Ausubel F M, (1994). *Current Protocols in Molecular Biology*. Chichester: John Wiley and Sons.

Antibodies or antibody fragments include those that are specific or preferentially selective for at least one HER2 form, and preferentially can be used to detect a soluble form of the HER2 protein. A soluble HER2 protein can have a molecular weight of about 185 kDa, as measured by gradient polyacrylamide gel electrophoresis. The soluble HER2 antigen can be an extracellular domain of HER2. The soluble HER2 antigen of the present invention can be part of a cell fragment or in any non-cellular lipid bilayer. See also U.S. Pat. No. 4,933,294 issued Jun. 12, 1990; WO91/05264 published Apr. 18, 1991; U.S. Pat. No. 5,401,638 issued Mar. 28, 1995, and Sias et al., *J Immunol Methods* 132:73-80 (1990), all herein incorporated by reference in their entirety. In an aspect, a soluble or shed HER2 antigen of the present invention is phosphorylated.

In another aspect of the present invention, antibodies or antibody fragments can be used to detect a secreted form of HER2. In another aspect of the present invention, antibodies or antibody fragments can be used to detect a soluble and secreted form or forms of HER2. In another aspect of the present invention, antibodies or antibody fragments can preferentially be used to detect the HER2 epitopes or fragments thereof, such as any of SEQ ID NOs: 10-18, which may be phosphorylated, such as at a tyrosine residue.

In one aspect of the present invention, an antibody or antibody fragment is capable of preferentially binding to a soluble form of HER2 protein. In this aspect, such preferential binding to HER2 can be relative to any other protein. In a particular aspect, such preferential binding to HER2 is relative to HER2 that is membrane bound or associated. In another particular aspect, such preferential binding to HER2 is relative to HER2 that is nuclear membrane bound or associated, e.g. nuclear membrane staining with a HER2 antibody of the present invention is less than the staining of a plasma membrane of the same cell.

In one aspect of the present invention, an antibody or antibody fragment is capable of preferentially binding to a secreted form of HER2 protein. In another aspect of the present invention, an antibody or antibody fragment is capable of binding to a secreted and soluble form or forms of HER2 protein. In another aspect of the present invention, an antibody or antibody fragment is capable of binding to HER2 epitopes of the present invention or fragments thereof.

As used herein, a membrane associated protein is a protein that can be found localized with a membrane upon examination of cell. A membrane bound protein is one that interfaces at least in part with the lipid bilayer. In one aspect, it is bound to the membrane via ionic interactions. In another aspect, a membrane bound protein is bound to the membrane via covalent interactions. In a preferred aspect, a membrane bound protein is bound to the membrane via hydrophobic interactions.

In an aspect of the present invention, preferential binding is relative to background. In another aspect, the preferential binding is at least 2-fold, 3-fold, 4-fold, 5-fold, 10-fold, 100-fold, 1,000-fold, 10,000-fold or 1,000,000-fold. In another aspect, an antibody of the present invention preferentially binds a soluble form of HER2 compared to a membrane form of HER2. In a particular aspect, an antibody of the present invention preferentially binds a soluble form of HER2 compared to a nuclear membrane form of HER2, or the reverse, in another aspect. A binding of the antibody can be measured in any way, and a preferred methodology is a gel-shift assay, set forth in Ausubel.

In an aspect, an antibody or antibody fragment binds HER2 or a particular form of HER2 such as a soluble form or a membrane bound form with a specific affinity of greater than $10^{-7}$M, $10^{-8}$M, $10^{-9}$M, $10^{-10}$M, or $10^{-11}$M, between $10^{-8}$M-$10^{-11}$M, $10^{-9}$M-$10^{-10}$ M, and $10^{-10}$ M-$10^{-11}$ M. In a preferred aspect, specific activity is measured using a competitive binding assay as set forth in Ausubel.

In another aspect, normal, non-metastatic and metastatic breast cancer epithelial cell images can be scored from 0 to +3 according to guidelines in HER2 Immunohistochemistry, Tissue Microarray Survey, Her2-A 2010, from the College of American Pathologists (CAP/ASCO Testing guidelines). See also Wolff, A C, et al., *Arch. Pathol. Lab. Med.* (2007) 131: 18-43. A score of "0" can be directed to no staining observed in invasive tumor cells. A score of "1+" can be directed to weak, incomplete membrane staining in any proportion of invasive tumor cells, or weak, complete membrane staining in less than 10% of cells in the sample. A score of "2+" can be complete membrane staining that is non-uniform or weak but with obvious circumferential distribution in at least 10% of cells, or intense complete membrane staining in 30% or less of tumor cells. A score of "3+" can be uniform intense membrane staining of more that 30% of invasive tumor cells. Intense staining can be easily visualized with 4× or 10× objective. Weak staining can require 40× objective for visualization.

One aspect of the present invention includes a method of diagnosing colon cancer by detecting HER2 with an antibody of the present invention. Another aspect of the present invention includes a method of diagnosing colon cancer by detecting HER2 with an antibody of the present invention. Using a HER2 antibody of the present invention, colon or stomach cancer is detected as +1 to +3 in a patient with colon cancer or stomach cancer. In another aspect, levels of ER are correlated to staining using a HER2 antibody of the present invention, such as Alper-HER2 mAb 2HE.

In one aspect of the present invention, the difference in immunohistochemical staining between the tissue specimens indicates that patients may have amyloid deposits in vascular walls (amyloid angiopathy) and that HER2 antigen may co-occur with amyloid deposits. In an aspect, an antibody or antibody fragment co-localizes with an amyloid protein. In another aspect, an antibody of the present invention is an antibody capable of preferentially binding to a soluble form of HER2 antigen. In another aspect, an antibody of the present invention is Alper HER2 moab 2HE antibody. In another aspect, an antibody or antibody fragment of the present invention can be used to detect breast cancer in a breast tissue of a subject.

A further aspect of the present invention provides a composition comprising: a tissue specimen, an antibody-antigen complex between an antibody capable of preferentially binding to a soluble form of HER2 antigen and a soluble form of HER2 antigen within the said specimen. In one aspect of the invention, the tissue specimen is preferably from a patient suffering from a disease characterized by the expression of gene products of HER2 and homologues thereof. In a further aspect of the invention, the patient is suffering from breast cancer, ovarian cancer, lung cancer, prostate cancer, or head/neck cancer. In another aspect of the invention, the soluble form of HER2 antigen is overexpressed in said tissue specimen. In one aspect, said antibody is Alper-HER2 monoclonal antibody 2HE. Another aspect of the invention provides a use of said composition for detecting a disease in a patient characterized by the expression of gene products of HER2 and homologues thereof. In one aspect of the invention, immunohistochemical staining of said composition indicates the presence of a disease in the patient. In one aspect of the invention, said disease is breast cancer, ovarian cancer, lung cancer, prostate cancer, or head/neck cancer. In another aspect, the disease is breast cancer, stomach cancer, colon cancer. In an aspect, it is breast cancer.

In an aspect, a HER2 antibody of the present invention, such as Alper-HER2 mAb 2HE, can identify a subset of HER2-positive cancer cells (metastatic or nonmetastatic) that are likely to benefit from treatment, such as with Herceptin®. Such a HER2 antibody of the present invention can be used in a method of identifying a subject in need thereof, such as a HER2-positive patient, that will preferentially benefit from treatment, including treatment with Herceptin®. In another aspect, a HER2 antibody of the present invention, such as Alper-HER2 mAb 2HE, can identify a subset of HER2-positive cancer cells (metastatic or nonmetastatic) that are likely to survive a significantly longer time than those HER-positive patients not in the subset identified by the HER2 antibody of the present invention. Such a HER2 antibody of the present invention can be used in a method of predicting survival for a subject in need thereof, such as a HER2-positive patient. Methods of the present invention can include a method of detecting lower levels of HER2 in blood, plasma, or sera using a HER2 antibody of the present invention. In an aspect, the method and detects HER2 earlier in the course of disease in plasma than currently commercially available tests.

Antibodies and antibody fragments can optionally be immobilized on a solid phase, detectably labeled, or conjugated to a cytotoxic radionuclide, a cytotoxic drug, or a cytotoxic protein and the like.

Antibodies and antibody fragments of the present invention can target expression of HER2 antigen by cells, preferably human cells, more preferably human cancer cells, such as solid tumors of human breast, ovary, cervix, prostate, colon, stomach, kidney, liver, head, neck, lung, blood, pancreas, skin, testicle, thyroid and brain cancer cells, most preferentially human breast, stomach and colon, in particular human breast cells. Expressed HER2 antigens can include any form of the gene product, although particularly preferred aspects relate, to the detection of the soluble or secreted form of HER2. Such antigens can also include gene produced homologues of the HER2 gene and modified HER2 antigens expressed by cancer cells.

Figure 2A:
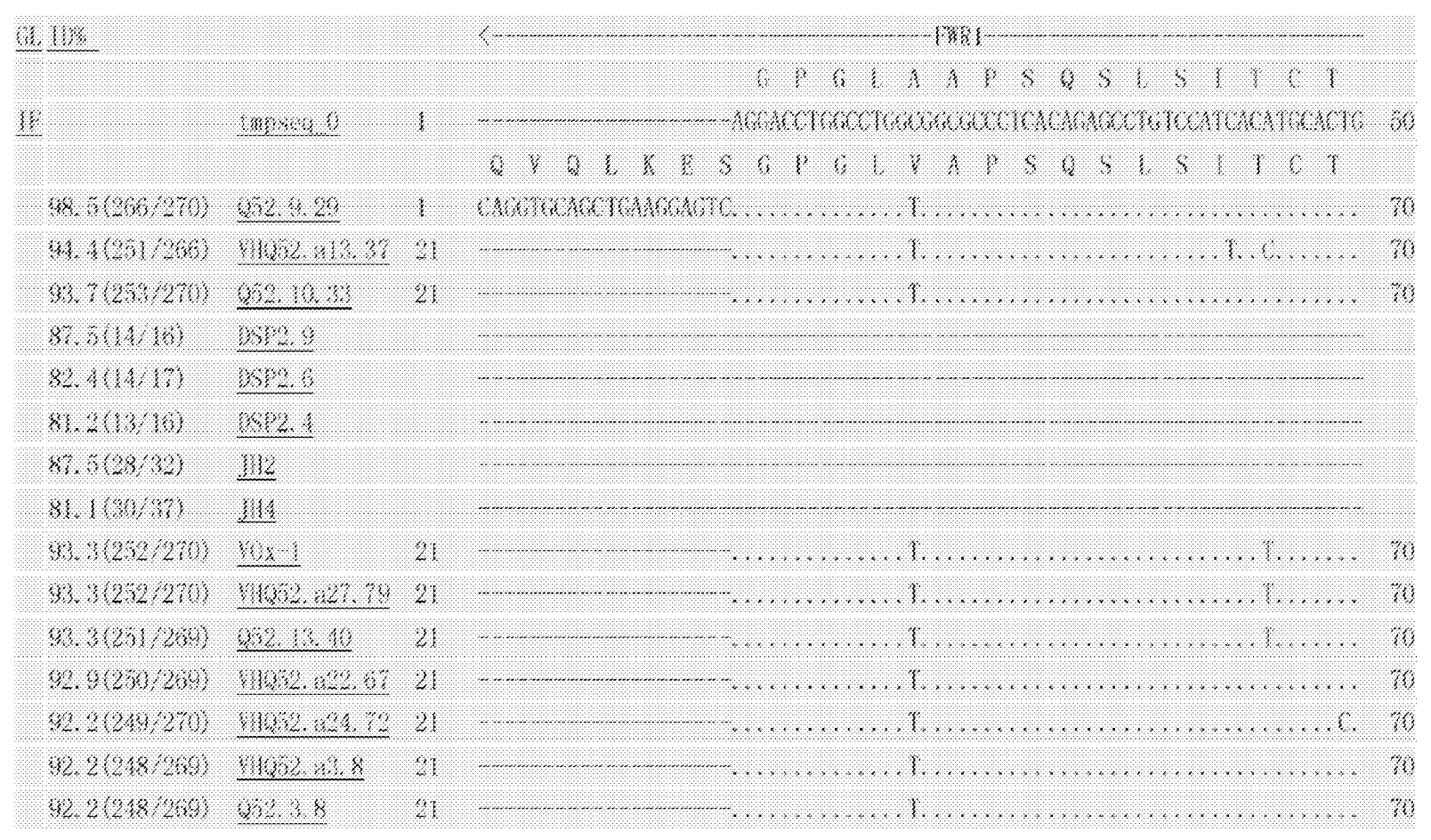
Figure 2B:
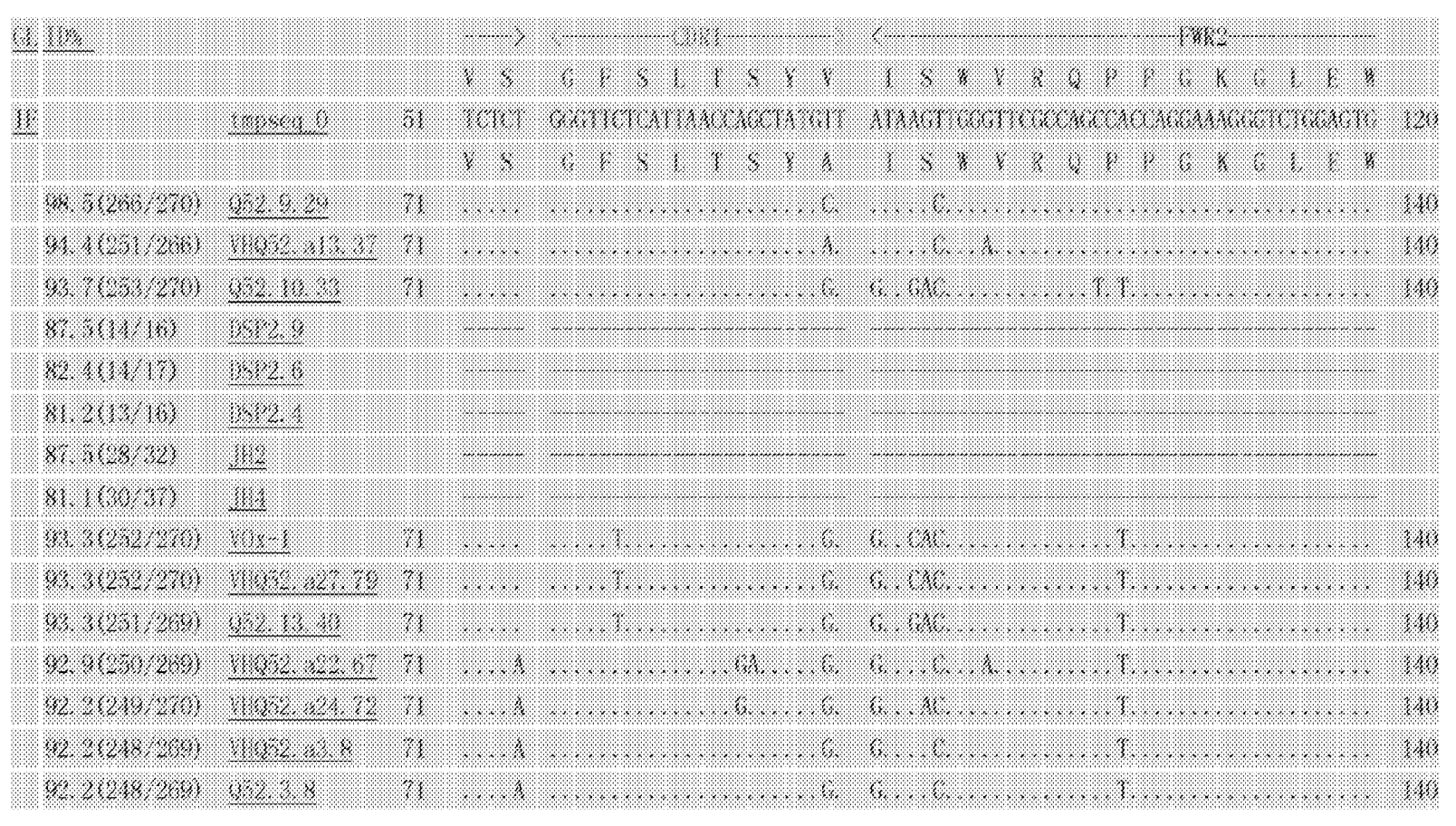
Figure 2C:
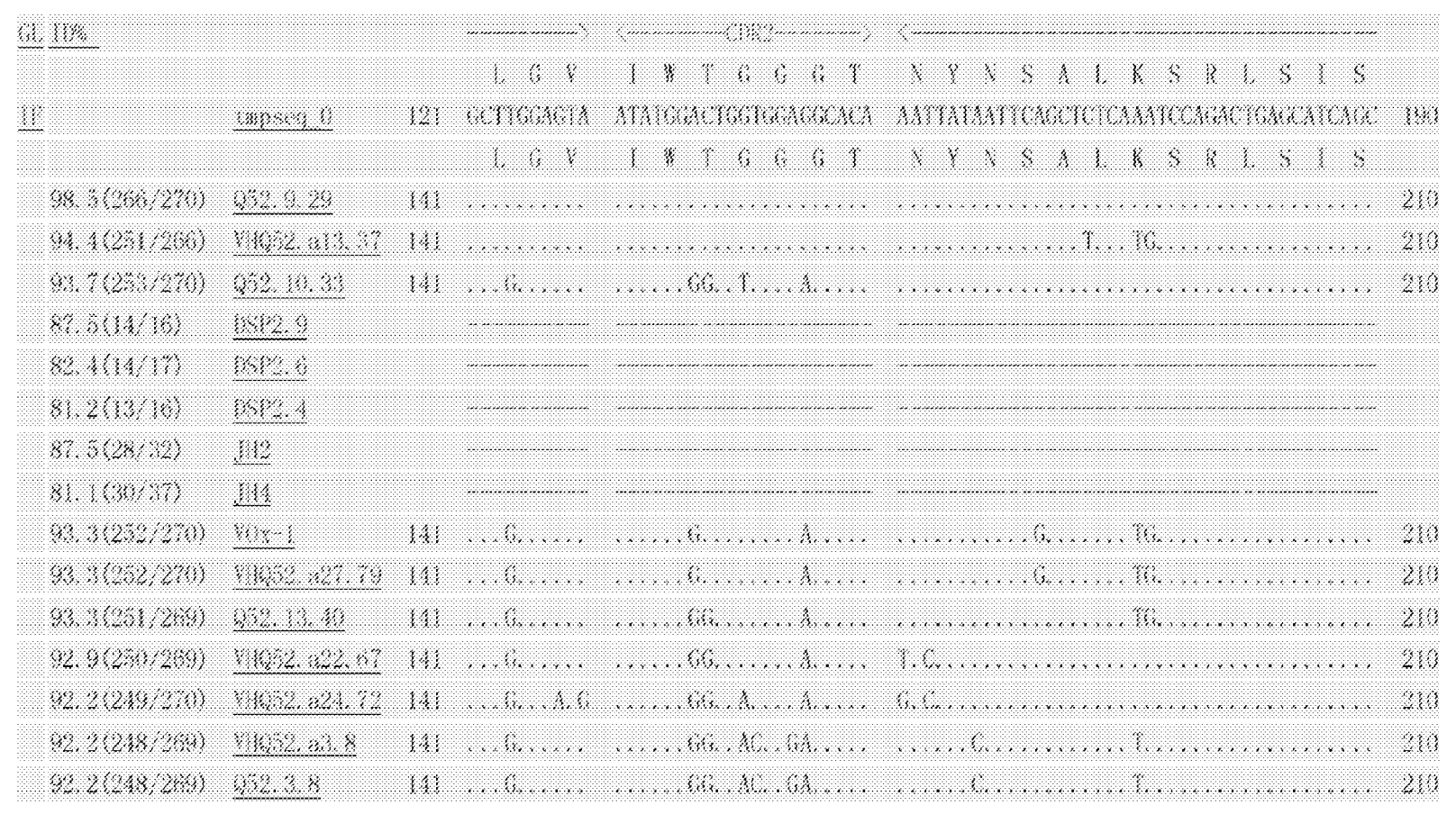
Figure 2D:
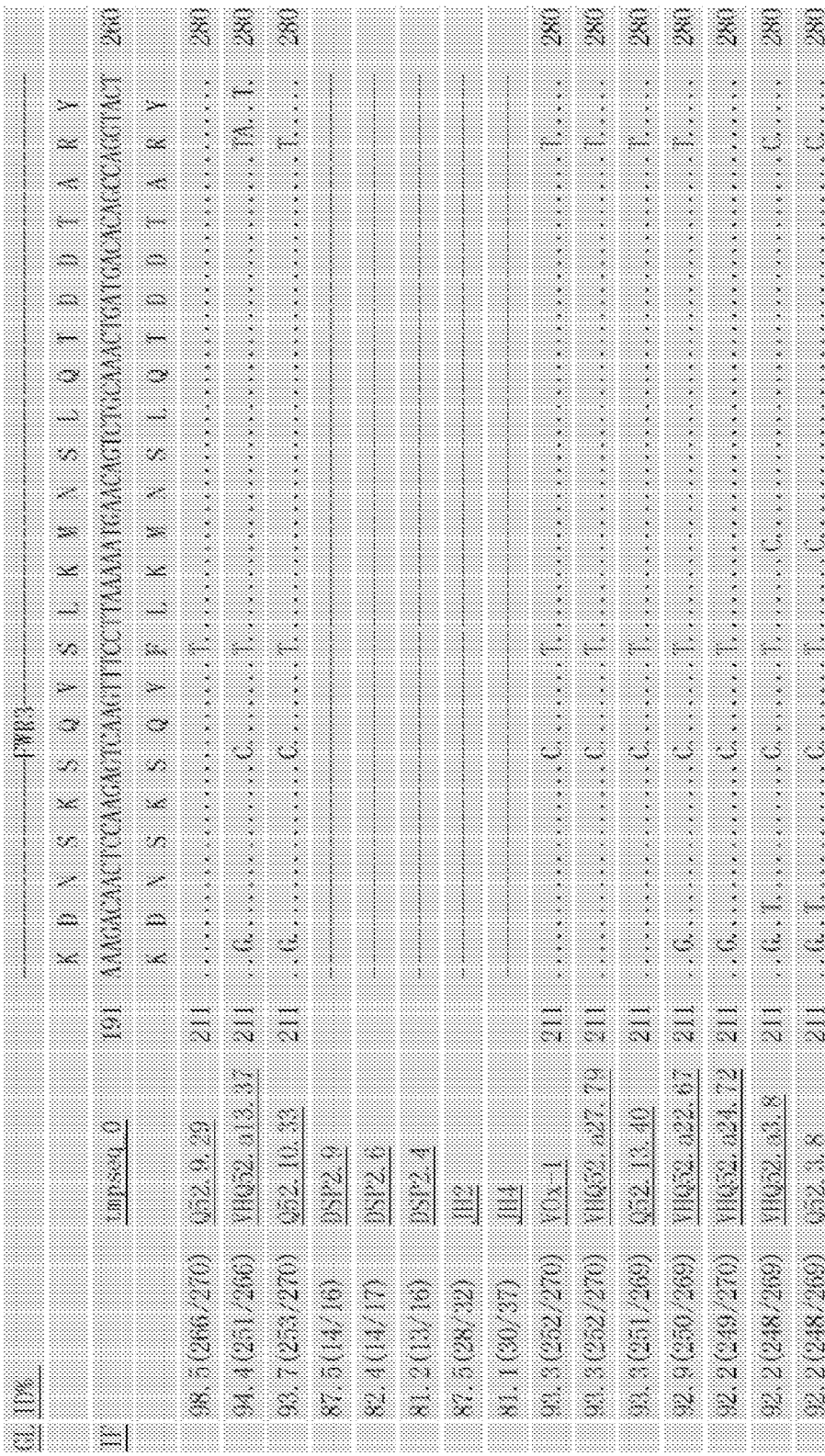
Figure 2E:
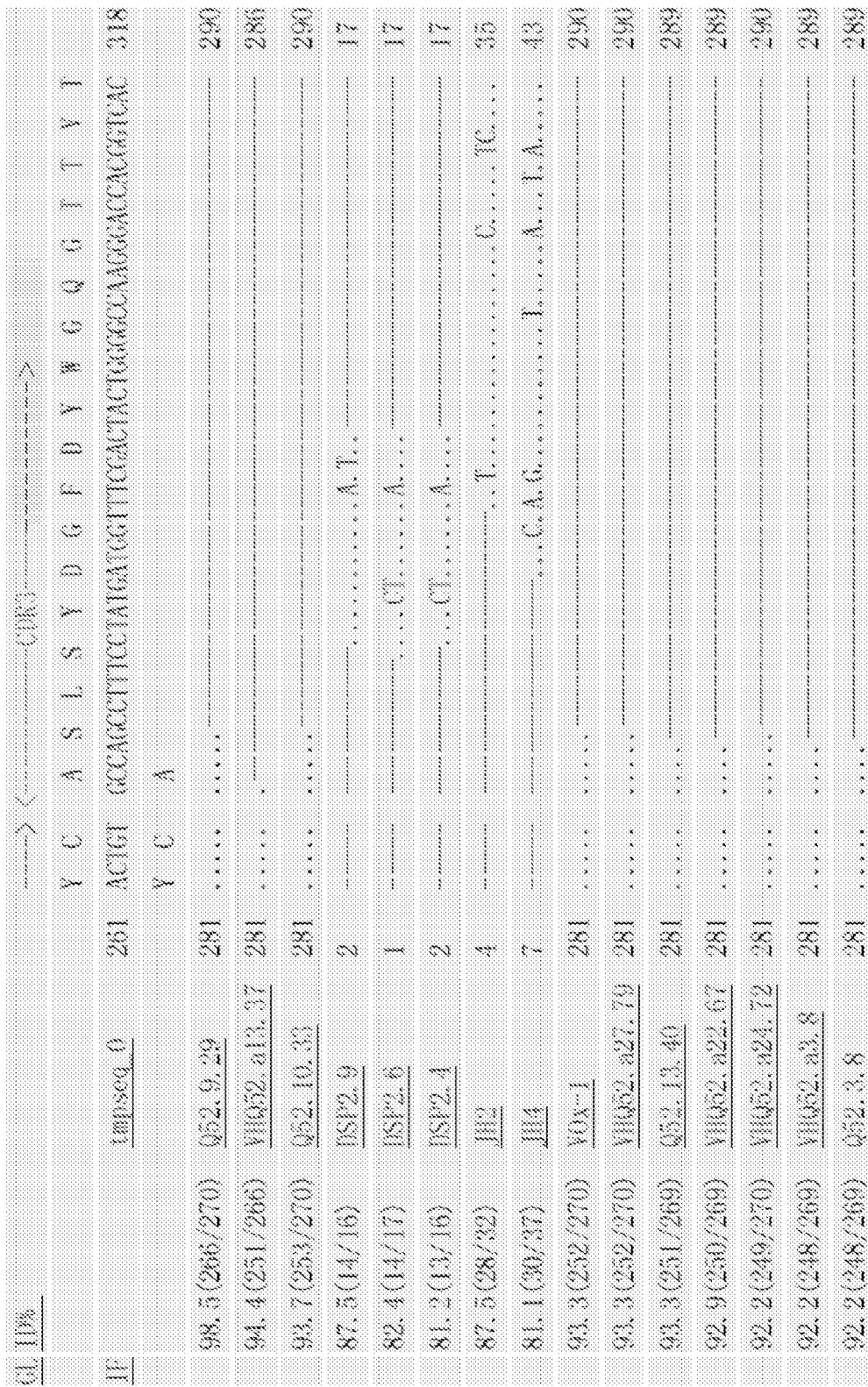
Figure 3A:
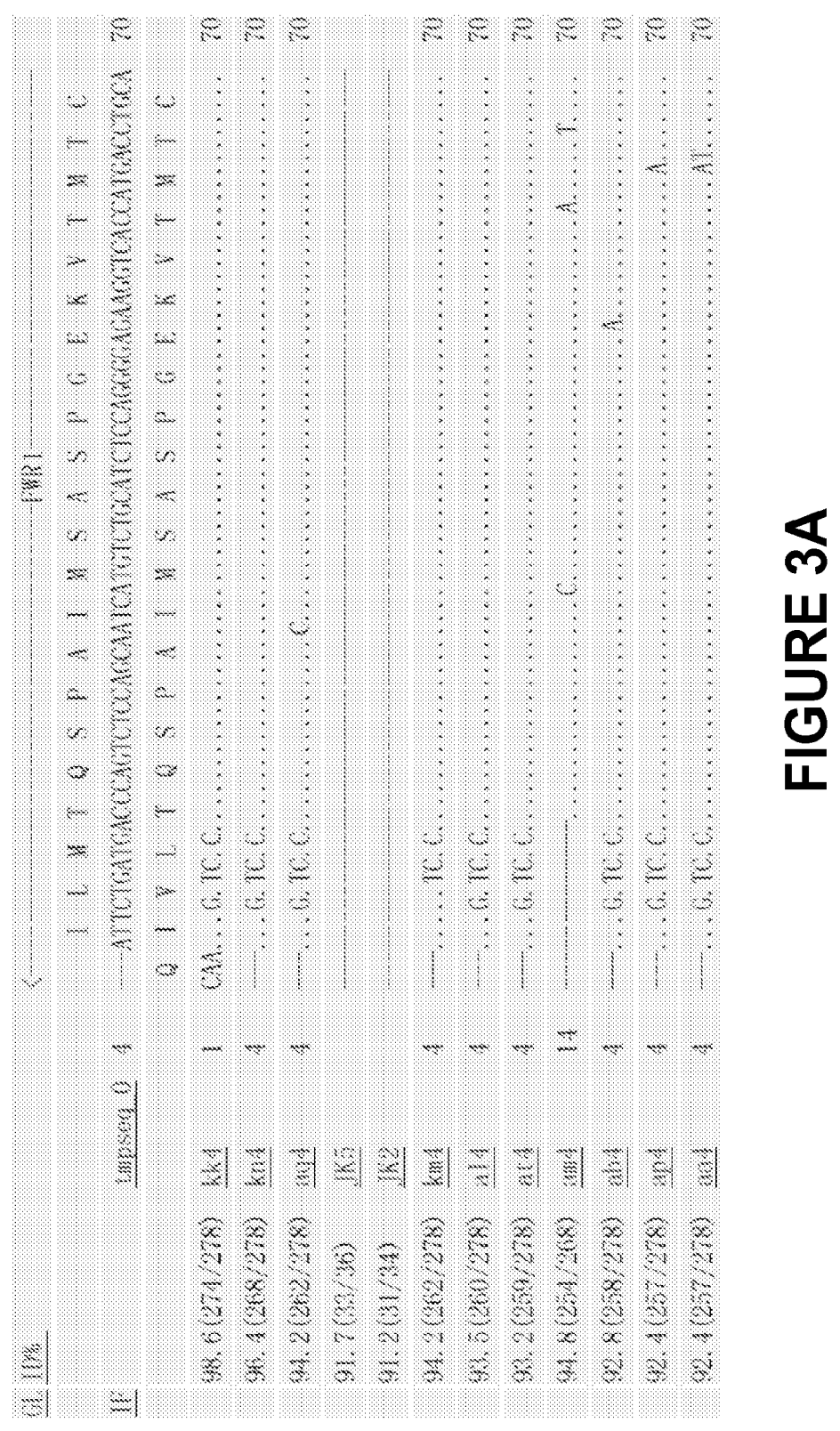
Figure 3B:
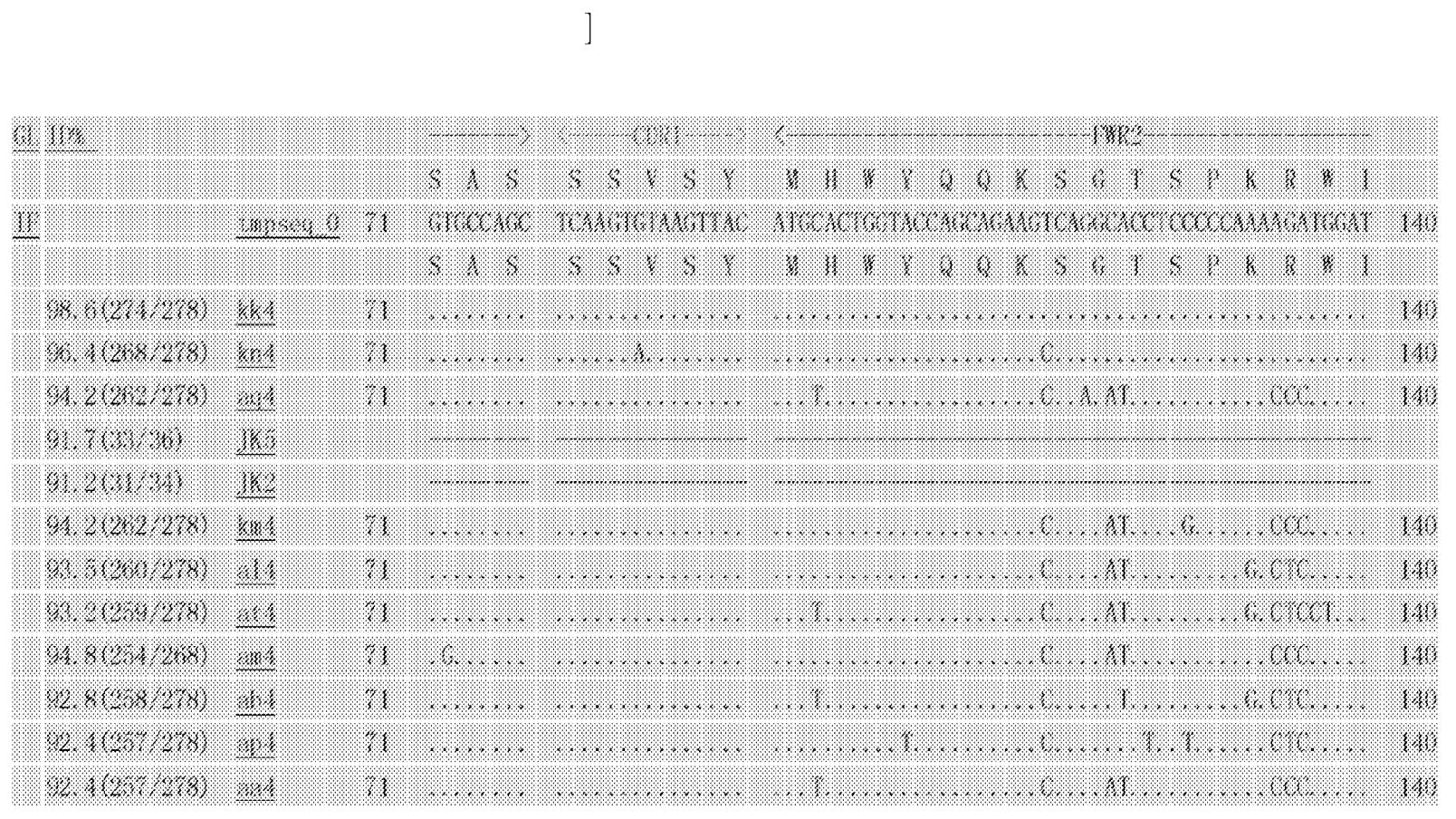
Figure 3C:
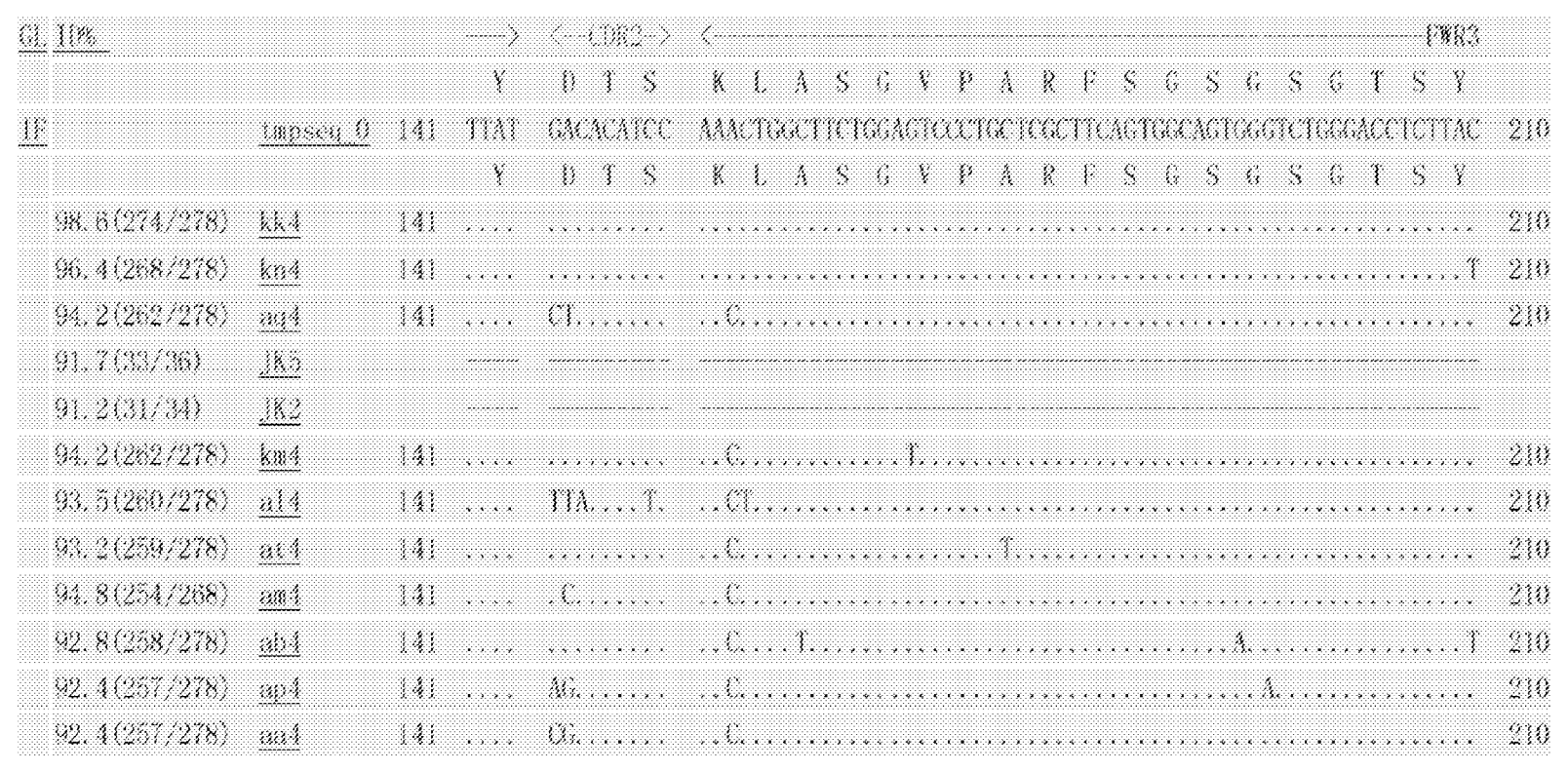
Figure 3D:
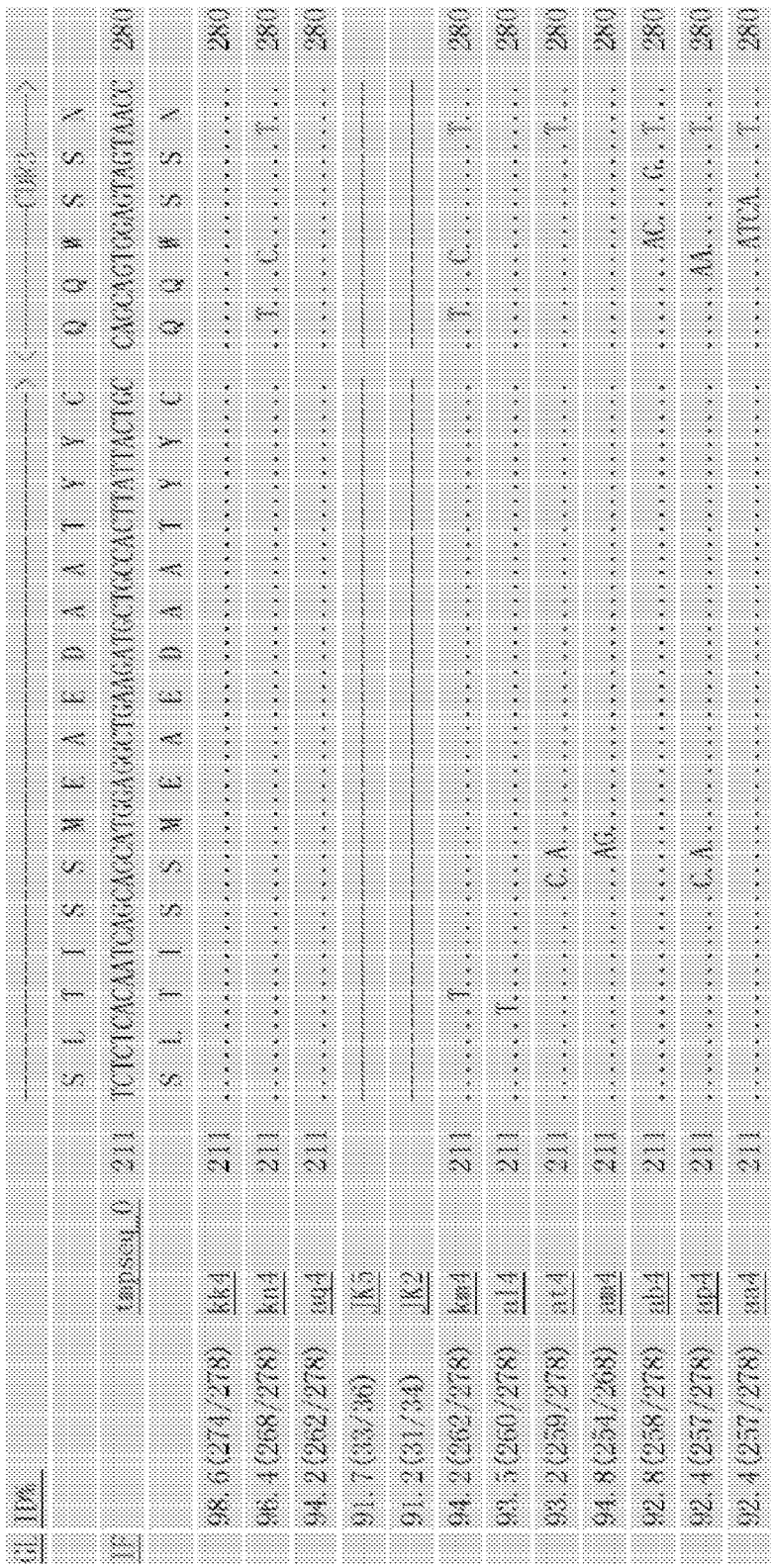
Figure 3E:
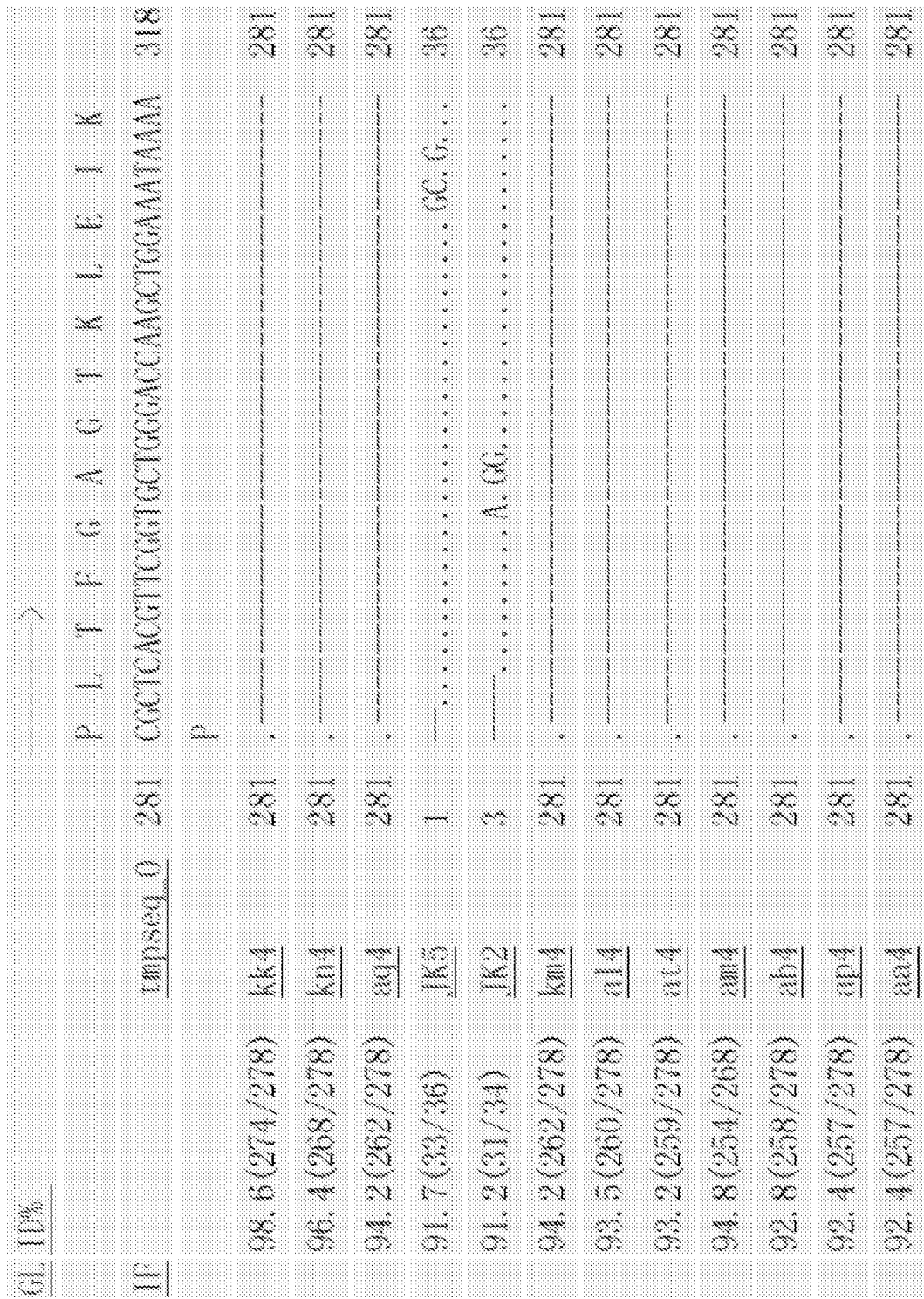

In an aspect, the present invention includes an antibody or an antibody fragment with preferential binding for a HER2 antigen, including the heavy chain CDR antigen binding site amino acid sequences CDR1, CDR2, and CDR3 as set forth in FIG. 2, and the light chain CDR antigen binding site amino acid sequences CDR1, CDR2 and CDR3 as set forth in FIG. 3. The present invention also includes an antibody with preferential binding for a HER2 antigen, comprising one or more of the heavy chain CDR antigen binding site amino acid sequences set forth in FIG. 2, and one or more of the light chain CDR antigen binding site amino acid sequences set forth in FIG. 3.

The present invention includes HER2 antibodies or antibody fragments having antigen binding sites with one or more of CDR1, CDR2, and CDR3, from both heavy and light chains, as described in FIGS. 2 and 3. The invention also includes antibodies and antibody fragments specific to HER2 expression products that contain antigen binding sites that are substantially homologous to these, or that result in substantially similar binding properties. Such antibodies or fragments thereof can be 95%, 90%, 85%, or 80% identical to one or more of the CDR1, CDR2, or CDR3 heavy or light chain from Alper-HER2 mAb (2HE). In an aspect, it can be 95% identical. The present invention also includes new hybridoma lines, and the monoclonal antibody molecules that they secrete, which are specific to HER2 antigen expressed by normal or cancer cells. The present invention also includes chimeric, such as humanized antibodies, and antibody fragments and also includes other modified antibodies and antibody fragments.

In addition to the specific amino acid sequences of the antigen binding sites of the heavy and light chains set forth in FIGS. 2 and 3, the present invention also encompasses antibodies and antibody fragments that have preferential binding to HER2 antigens but which have FWR and/or CDR antigen binding site amino acid sequences that are not identical to those set forth in FIGS. 2 and 3. Such antibodies and antibody fragments are preferred if they are specific or preferentially selective for the HER2 antigen, preferably at least 2-fold, at least 5-fold, at least 10-fold or at least 50-fold higher affinity for the HER2 antigen as the Alper-HER2 mAb (2HE) or antibody fragment thereof. According to a preferred aspect, a variant of an antibody or antibody fragment of the present invention can be as specific for the HER2 antigen as a non-variant antibody or antibody fragment of the present invention, or can be more specific.

Antibodies and antibody fragments that are specific to HER2 but which have FWR and/or CDR antigen binding site amino acid sequences that are not identical to those set forth in FIGS. 2 and 3 can possess the same or different specificity determining regions (SDRs) as the FWRs and/or CDRs of FIGS. 2 and 3 are included (set forth in bold, underlined text in these figures).

Modifications to the amino acid sequences set forth in FIG. 2 (heavy chain) and FIG. 3 (light chain) can occur in either or both of the FWR and CDR sequences. In an aspect, modifications can be made to another HER2 antibody to match one or more amino acid sequence of the antigen binding sites CDR1, CDR2, and CDR3 set forth in FIG. 2 (heavy chain) and FIG. 3 (light chain). According to certain aspects of the invention, variations in antibodies or antibody fragments can occur where they have substantially homologous amino acid sequences, antibodies having substantially similar binding properties, or both. In one aspect of the invention, there can be a single amino acid change in the CDR antigen binding sites. In one aspect of the invention, there can be a single amino acid change in the CDR1 antigen binding site. In one aspect, the single amino acid change is at residue number 26. Included in the present invention, is a non-Alper HER2 moab 2HE antibody that binds HER2 and is modified to have a valine at a residue corresponding to the Alper HER2 moab 2HE residue number 26. In another aspect of the present invention, there can be no amino acid changes in the CDR antigen binding sites. According to one aspect of the invention, a commercial antibody is provided that has a single amino acid change in the CDR1 antigen binding site. In another aspect, the amino acid substitution may be at an amino acid residue other than the one denoted in the sequence listing.

Amino acid sequence variants of the HER2 antibody are prepared by introducing appropriate nucleotide changes into the HER2 antibody nucleic acid, or by peptide synthesis. Such modifications include, for example, deletions from, and/or insertions into and/or substitutions of, residues within the amino acid sequences of the HER2 antibody. Any combination of deletion, insertion, and substitution is made to arrive at the final construct, provided that the final construct possesses the desired characteristics. The amino acid changes also may alter post-translational processes of the HER2 antibody, such as changing the number or position of glycosylation sites.

Amino acid substitution variants have at least one amino acid residue in the HER2 antibody molecule replaced by a different residue. The sites of greatest interest for substitutional mutagenesis include the hypervariable regions or CDRs, but alterations in FWR regions are also contemplated.

Conservative substitutions involve replacing amino acids with those that have similiar charge or hydrophobicity, for example:

(1) non-polar: Ala (A), Val (V), Leu (L), Ile (I), Pro (P), Phe (F), Trp (W), Met (M);

(2) uncharged polar: Gly (G), Ser (S), Thr (T), Cys (C), Tyr (Y), Asn (N), Gln (Q);

(3) acidic: Asp (D), Glu (E);

(4) basic: Lys (K), Arg (R), H is (H).

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: H is, Lys, Arg;

(5) residues that influence chain orientation: Gly, Pro;

(6) aromatic: Trp, Tyr, Phe.

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated.

Humanized variants of the antibodies or antibody fragments of the invention can contain a reduced murine content, and potentially, reduced immunogenicity, when compared to murine antibodies, such as Alper-HER2 mAb (2HE), or antibody fragments thereof. Humanized variants include those that retain a binding affinity that is substantially similar to that of the original antibody or antibody fragment. An aspect of the invention provides CDR variants of humanized HER2 antibodies or antibody fragments in which 1, 2, 3, 4, 5, or 6 (three heavy chain and three light chain) CDRs are humanized. A second aspect of the invention provides SDR variants of humanized HER2 antibodies and antibody fragments in which only Specificity Determining Residues (SDRs) of at least one CDR from the HER2 antibodies and antibody fragments are present in the humanized antibodies. The SDRs are selected from Table 1 or Table 2. In an aspect of the present invention, the CDRs are listed in the sequence listing and FIGS. 2 and 3. CDR2 of the light chain is amino acid sequence DTS.

TABLE 1

Specificity-Determining Residues in Alper-HER2 mAb (2HE) Heavy Chain (SEQ ID NO. 1)

| Position | Residue |
|---|---|
| 5 | A |
| 26 | V |
| 72 | S |

TABLE 2

Specificity-Determining Residues in Alper-HER2 mAb (2HE) Light Chain (SEQ ID NO. 5)

| Position | Residue |
|---|---|
| 2 | L |
| 3 | M |

CDR variants can be formed by replacing at least one CDR of a humanized HER2 antibody and antibody fragments with a corresponding CDR from a human antibody. CDR variants in which one, two, three, four, five, or six CDRs are replaced by a corresponding CDR from a human antibody and retain biological activity that is substantially similar to the binding affinity of the parental HER2 mAb. CDR variants of the invention can have a binding affinity that is 25% more than the binding affinity of the parental HER2 antibody or antibody fragment, more preferably is more than 50%, most preferably at least 75% or 90%.

CDR variants can have altered immunogenicity when compared to HER2 antibodies and antibody fragments can be formed by grafting all six (three heavy chain and three light chain) CDRs from the HER2 antibodies and antibody fragments of the present invention onto the variable light ($V_L$) and variable heavy ($V_H$) frameworks of human antibodies and antibody fragments. However, less than all six of the CDRs of the HER2 antibodies and antibody fragments of the present invention can be present, while still permitting an antibody of the present invention to retain activity. Residues that are directly involved in antigen contact, such as Specificity Determining Residues (SDRs), can be refined. SDR variants are formed by replacing at least one SDR of the HER2 antibody or antibody fragment with a residue at a corresponding position from a human antibody. It should be noted that not all CDRs must include SDRs.

In a preferred aspect, the variants of the present antibodies and antibody fragments include a combination of CDR and/or SDR substitutions to generate variants having reduced immunogenicity in humans and a binding affinity that is substantially similar to that of the parental antibody or antibody fragment to HER2.

In addition to variants specifically described herein, other "substantially homologous" modified immunoglobulins can be readily designed and manufactured using various recombinant DNA techniques. For example, the framework regions (FWRs) can be varied at the primary structure level. Moreover, a variety of different human framework regions can be used singly or in combination as a basis for the variant. In general, modifications of the genes can be readily accomplished by a variety of techniques, such as site-directed mutagenesis and random mutagenesis.

Alternatively, polypeptide fragments comprising only a portion of the primary antibody structure can be produced where the fragment substantially retains the immunoreactivity properties of the variant. Such polypeptide fragments include fragments produced by proteolytic cleavage of intact antibodies or fragments produced by inserting stop codons at the desired locations nucleotide sequence using site-directed mutagenesis. Single chain antibodies and fusion proteins which include at least an immunoreactivity fragment of the variant are also included within the scope of the invention.

The antibodies and their variants in accordance with the present invention can be directly or indirectly attached to effector moieties having therapeutic activity. Suitable effector moieties include cytokines, cytotoxins, radionuclides, drugs, immunomodulators, therapeutic enzymes, anti-proliferative agents, etc. Methods for attaching antibodies to such effectors are known in the art. These conjugated antibodies can be incorporated into any composition, including pharmaceutical compositions for use in treating diseases characterized by the expression of HER2, including cancer, such as cancer of the breast, ovary, cervix, prostate, colon, stomach, kidney, liver, head, neck, lung, blood, pancreas, skin, testicle, thyroid and brain, most preferentially human breast, ovary, head, neck, and brain, in particular human breast cells. The pharmaceutical compositions are preferably administered to a mammal, more preferably a human patient in need of such treatment, in order to treat the disease.

Antibodies and antibody fragments can either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels can be employed, such as radionuclides, fluors, enzymes, enzyme substrates, enzyme cofactors, enzyme inhibitors, ligands (particularly haptens), etc. Numerous types of immunoassays are available.

3. Nucleic Acid Molecules and Host Cells

Any of the antibodies or antibody fragments of the present invention can be encoded by nucleic acids. The present invention includes such molecules, fragments of such molecules and such molecules included in vectors and the like. Nucleic acid molecules also include the complement of such nucleic acid molecules. Both DNA and RNA molecules are examples of nucleic acid molecules.

In another aspect, the present invention provides an isolated DNA sequence which encodes the heavy chain of an antibody molecule, where the antibody molecule has preferential binding for HER2 antigens, including at least HER2, and where the variable domain of the heavy chain comprises a CDR having the antigen binding site amino acid sequences of at least one, two or all three CDR1, CDR2, and CDR3 set forth in FIG. 2.

In yet another aspect, the present invention provides an isolated DNA sequence which encodes the light chain of an antibody molecule, where the antibody molecule has preferential binding for HER2 antigens, including at least HER2, and further where the variable domain of the light chain comprises a CDR having the antigen binding site amino acid sequences of at least one, two or all three CDR1, CDR2, and CDR3 set forth in FIG. 3.

In another aspect, the present invention includes a nucleic acid molecule in a host cell. Such nucleic acid molecule can be integrated into the genome of the host cell or can be present on a vector such as a plasmid or viral vector. A nucleic acid molecule of the present invention may be transiently present in such a host cell. In one aspect, a host cell is selected from the group *E. coli; Bacilli*, including *Bacillus subtilis*; enterobacteriacae, including *Salmonella, Serratia* and *Pseudomonas*, yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines. In one aspect, a host cell is selected from a breast cancer cell line such as SKBR3, MCF-7, MDA-MB-231, MDA-MB-435, and ZR75B cells. In another aspect, a host cell is selected from a prostate cancer cell line such as PC3, DU145 and LNCap cells. In another aspect, a host cell is selected from a colon cancer cell line such as HT-29 cells. In another aspect, a host cell is selected from a skin cancer cell line such as A431 cells. In another aspect, a host cell is selected from a kidney cancer cell line such as BHK-21 or COS-7 cells. In another aspect, a host cell is selected from an ovarian cancer cell line such as A2780, A2780ADR, or A2780cis cells. In another aspect, it is a CHO cell.

4. Methods of Making HER2 Antibodies or Antibody Fragments

HER2 antibodies or antibody fragments of the present invention can be developed, for example, using the human breast cancer cell line SKBR3 (available from the American Type Culture Collection as ATCC No. HTB30).

The present invention includes processes for producing monoclonal, chimeric, including humanized antibodies using recombinant DNA technology. See, for example, *Antibodies, A Laboratory Manual* (Harlow & Lane Eds., Cold Spring Harbor Press, 1988), which is herein incorporated by reference in its entirety.

HER2 antibodies or antibody fragments of the present invention can be produced by any known method including, without limitation, generating murine hybridomas which produce antibodies or antibody fragments specific for HER2. Hybridomas can be formed, for example, by the fusion of a mouse fusion partner cell and spleen cells from mice immunized against native HER2 prepared without fixation. Mice can be also immunized with crude or semi-purified preparations containing an antigen of interest, such as a native HER2 isolated without fixation. To immunize the mice, a variety of different conventional protocols can be followed. For example, mice can receive primary and boosting immunizations of antigenic preparations.

Cell fusions can be accomplished by any procedures known to those skilled in the field of immunology. Fusion partner cell lines and methods for fusing and selecting hybridomas and screening for antibodies or antibody fragments are known.

Antibodies or antibody fragments of the present invention can be produced in large quantities, for example, by injecting hybridoma cells secreting the antibody into the peritoneal cavity of mice and, after appropriate time, harvesting the ascites fluid which contains a high titer of the antibody or antibody fragment, and isolating the antibody or antibody fragment therefrom. Alternatively, the antibodies and antibody fragments can be produced by culturing hybridoma cells in vitro and isolating the secreted antibody or antibody fragment from the cell culture medium.

HER2 antibodies or antibody fragments of the present invention can also be produced by expressing the appropriate DNA sequence in a host after the sequence has been operably linked to an expression control sequence. Such expression vectors are often replicable in a host organism either as episomes or as an integral part of the host chromosomal DNA. Expression vectors often contain expression control sequences compatible with the host cell, such as an origin of replication. In addition, an expression vector can include a promoter to control expression of the gene, optionally, with operator sequences, and have ribosome binding site sequences and the like for initiating and completing transcription and translation. Suitable promoters include, without limitation, the polyhedrin promoter, lactose promoter system, a tryptophan promoter system, a beta-lactamase promoter system, or a promoter system from phage lambda. Expression vectors can also contain selection markers. DNA sequences encoding the light chain and heavy chain of an HER2 antibody or antibody fragments can be inserted into separate expression vectors, or into the same expression vector.

Suitable hosts include, without limitation, prokaryotic strains such as *E. coli*; Bacilli, including *Bacillus subtilis*; enterobacteriacae, including *Salmonella, Serratia* and *Pseudomonas*. Suitable hosts also include eukaryotic hosts such as yeast, including *Saccharomyces; Pichia pastoris*; Sf9 insect cells; Sp2/0, VERO and HeLa cells, Chinese hamster ovary (CHO) cell lines; W138, BHK, COS-7 and MDCK cell lines. Other suitable hosts can also be used in accordance with known expression techniques.

The vectors containing the DNA segments of interest can be transferred into the host cell by any method, which varies depending on the type of cellular host. For example, calcium chloride transfection, calcium phosphate treatment, electroporation or cationic liposome mediated transfection (such as DOTAP). Successfully transformed cells, can be identified by a variety of techniques for detecting the binding of a receptor to a ligand.

Expressed gene products can be purified according to any method, including, without limitation, ammonium sulfate precipitation, affinity columns, column chromatography, and gel electrophoresis. Substantially pure immunoglobulins of at least 80% homogeneity are preferred, with about 90% to about 95% homogeneity being more preferred, and 98% to 99% or more homogeneity is most preferred, and is generally considered acceptable for pharmaceutical uses.

Isolated or purified DNA sequences can be incorporated into a cloning or expression vector, which can in turn be used to transform a host cell. The transformed host cells can be used in a process for the production of an antibody molecule having specificity for HER2 antigens, including culturing the host cells and isolating the antibody molecules they produce.

5. Diagnostic Methods, Assays, and Kits

In a further aspect, the present invention includes an immunoassay for preferentially detecting a HER2 antigen comprising an antibody or antibody fragment of the present invention.

The present invention also includes an immunoassay for preferentially detecting one or more HER2 antigens, including a HER2 antigen, which bind to a monoclonal antibody having one or more of the heavy chain CDR antigen binding site amino acid sequences set forth in FIG. 2, and one or more of the light chain CDR antigen binding site amino acid sequences set forth in FIG. 3.

Such immunoassays can be used in any suitable manner, including, without limitation, by comprising: (a) contacting the sample with an effective binding amount of one of the antibodies or antibody fragments of the invention; and (b) detecting the antigen by detecting the binding of the antibody to a HER2 antigen. Immunoassays of the present invention can be used to detect cancer cells expressing a HER2 antigen, particularly cancer, tumor, carcinoma cells or neoplastic disease cells selected from the group consisting of breast, ovarian, cervical, prostate, colon, stomach, kidney, liver, head, neck, lung, blood, pancreatic, skin, testicular, thyroid and brain cancers, most preferentially human breast, ovary, head, neck, and brain, in particular human breast cells.

In a further aspect, the present invention provides a kit for the immunohistochemical detection of carcinoma comprising: (a) an antibody or antibody fragment of the present invention; and (b) a secondary antibody conjugated to a detectable label.

In a further aspect, the present invention provides a kit for the immunohistochemical detection of carcinoma comprising: (a) a monoclonal antibody having one or more of the heavy chain CDR antigen binding site amino acid sequences set forth in FIG. 2, and one or more of the light chain CDR antigen binding site amino acid sequences set forth in FIG. 3; and (b) a secondary antibody conjugated to a detectable label.

Kits can include reagents for assaying a sample for a HER2 antigen, where such kits may include: HER2 antigen specific affinity reagents, such as an antibody, or fragment or mimetic thereof, and/or immunoassay devices comprising the same members of a signal producing system, such as antibodies, enzyme substrates, and the like; various buffers for use in carrying out the subject detection assays; a reference for determining the amount of one or more HER2 antigens in a sample; and the like. Other examples of kits or kit formats are found in Alper, US Publication No. 2008/0293162, herein incorporated by reference in its entirety.

In further aspect, the present invention provides a method for diagnosing cancer in humans comprising: (a) removing a specimen from a patient suspected of having a cancer; (b) contacting the specimen with an antibody or antibody fragment of the present invention; (c) labeling the specimen; and (d) detecting the presence of the antigen-antibody complex by the label. Such a method of diagnosing cancer can be performed in vivo or in vitro.

In a still further aspect, the present invention provides a method for diagnosing cancer in humans comprising: (a) removing a specimen from a patient suspected of having a cancer; (b) contacting the specimen with a monoclonal antibody having one or more of the heavy chain CDR antigen binding site amino acid sequences set forth in FIG. 2, and one or more of the light chain CDR antigen binding site amino acid sequences set forth in FIG. 3; (c) labeling the specimen; and (d) detecting the presence of the antigen-antibody complex by the label. The method of diagnosing cancer can be performed in vivo or in vitro.

The cancers being diagnosed include those that are selected from the group consisting of solid tumors of the breast, ovary, cervix, prostate, colon, stomach, kidney, liver, head, neck, lung, pancreas, skin, testicle, thyroid and brain, most preferentially human breast, ovary, head, neck, and brain, in particular human breast cells.

In an aspect, HER2 levels are higher in early-stage breast cancer patients relative to age-matched healthy controls. In another aspect, HER2 levels are higher in middle-stage breast cancer patients relative to age-matched healthy controls. In a third aspect, HER2 levels are higher in late-stage breast cancer patients relative to age-matched healthy controls. In one aspect, the levels of HER2 are higher in early-stage breast cancer patients relative to age-matched healthy controls, and similar to healthy control levels during the late stage of breast cancer. An increase in HER2 levels means that they are statistically significant relative to an age-matched healthy controls. Levels similar to healthy control levels can mean that the levels are not statistically significant. In an aspect, the statistically significant differences in levels of HER2 have a p-value of $p<0.05$ as measured by the Mann-Whitney test. In another aspect, the statistically significant differences in levels of HER2 have a p-value of $p<0.01$ as measured by the Mann-Whitney test. In a further aspect, the statistically significant differences in levels of HER2 have a p-value of $p<0.005$ as measured by the Mann-Whitney test. In a further aspect, the statistically significant differences in levels of HER2 have a p-value of $p<0.001$ as measured by the Mann-Whitney test.

In a further aspect, the present invention provides a method for diagnosing breast cancer in a subject in need thereof comprising: (a) contacting a specimen from said subject with an antibody or antibody fragment of the present invention; (b) labeling the specimen; and (c) detecting an increase of HER2 in a patient with breast cancer, where such breast cancer can be in early-stage, mid-stage, or late-stage. Such a method of diagnosing cancer can be performed in vivo or in vitro.

In a still further aspect, the present invention provides a method for diagnosing breast cancer in humans comprising: (a) removing a specimen from a patient suspected of having a cancer; (b) contacting the specimen with a monoclonal antibody having one or more of the heavy chain CDR antigen binding site amino acid sequences set forth in FIG. 2, and one or more of the light chain CDR antigen binding site amino acid sequences set forth in FIG. 3; (c) labeling the specimen; and (d) detecting the presence of the antigen-antibody complex by the label. The method of diagnosing cancer can be performed in vivo or in vitro.

The breast cancer being diagnosed can be any of early-, mid- or late-stage breast cancer a combination thereof.

In an additional aspect, the present invention includes a method for developing drugs useful in treating, diagnosing, or both treating and diagnosing diseases characterized by the expression of gene products of HER2 and homologues thereof, including identifying gene products expressed by HER2 and homologues thereof, and utilizing the gene products as biomarkers in the development and identification of drugs selected from the group consisting of HER2 antibodies and antibody fragments, inhibiting peptides, siRNA, antisense oligonucleotides, vaccines, and chemical compounds, which specifically target the gene products.

Another aspect of the invention provides an immunohistochemical method for detecting a disease in a patient which disease is characterized by the expression of gene products of HER2 and homologues thereof, comprising the steps of: (a) obtaining said tissue specimen, (b) contacting said tissue specimen with an antibody capable of preferentially binding a soluble form of HER2 antigen, (c) staining said tissue specimen with an immunohistochemical staining, and said staining indicating the presence of disease in a patient that is characterized by the expression of gene products of HER2 and homologues thereof. In one aspect, the disease is breast cancer, ovarian cancer, lung cancer, prostate cancer, or head/neck cancer. In further aspect of the invention, said antibody is Alper-HER2 monoclonal antibody 2HE. In one aspect of the invention, an antibody capable of preferentially binding a soluble HER2 antibody can be derived based on the structural information of Alper-HER2 monoclonal antibody 2HE disclosed in this specification according to skill in the art. In a further aspect, said tissue specimen is from breast. In one aspect, the immunohistochemical staining is any staining method known in the art, including but not limited to, H&E staining and silver staining.

An antibody or antibody fragment of the present invention can also be used in diagnosis of diseases characterized by the expression of HER2, such as cancer. For example, in vivo diagnosis and imaging of a solid tumor of the breast, ovary, cervix, prostate, colon, stomach, kidney, liver, head, neck, lung, blood, pancreas, skin, testicle, thyroid or brain and combinations thereof, most preferentially human breast, ovary, head, neck, or brain and combinations thereof, in particular human breast cells, that expresses HER2 can be performed in accordance with the methods of the invention. An antibody or antibody fragment of the present invention can also be used for diagnosis in vitro, for example, by using an antibody or antibody fragment to detect the presence of the cancer marker HER2 in a fluid or tissue sample.

Antibodies and antibody fragments can be used in immunoassays to screen body fluids, such as serum, sputum, effusions, urine, cerebrospinal fluid, and the like, for the presence of HER2. Antibodies and antibody fragments can be used for scanning or radioimaging, when labeled with an appropriate radiolabel, to detect primary or metastatic foci of tumor cells. Furthermore, the antibodies are useful in lymphoscintigraphy to detect lymph node involvement in the disease.

A HER2 antibody or antibody fragment, which can include any or all of the antibodies or antibody fragments specific for HER2-related gene products, and/or chimeric, such as humanized, or other variants thereof, can be used therapeutically, or in developing and performing assays, in vivo or in vitro diagnostic procedures, and imaging. The antibodies can be used alone or in combination with a pharmaceutically-acceptable or diagnostic carrier formulation. HER2 antibodies or antibody fragments can be incorporated into a pharmaceutically or diagnostically acceptable, non-toxic, sterile carrier as a suspension or solution. They can be used as separately administered compositions or given in conjunction with chemotherapeutic or immunosuppressive agents.

The present invention includes therapeutic and diagnostic compositions comprising an antibody or antibody fragment of the present invention in combination with a pharmaceutically acceptable excipient, diluent or carrier. The present invention also includes a process for preparation of a therapeutic or diagnostic composition comprising admixing an antibody molecule of the present invention together with a pharmaceutically acceptable excipient, diluent or carrier. An antibody molecule can be the sole active ingredient in the therapeutic or diagnostic composition, or can be accompanied by other active ingredients including other antibody ingredients, for example anti-T cell, anti-IFNγ or anti-LPS antibodies, or non-antibody ingredients such as xanthines. Compositions can be incorporated into kits for diagnosing or treating diseases characterized by the expression of HER2, including, without limitation, solid tumors, and particularly solid tumors of the breast, ovary, cervix, prostate, colon, stomach, kidney, liver, head, neck, lung, pancreas, skin, testicle, thyroid and brain, most preferentially human breast, ovary, head, neck, or brain, in particular human breast cells.

Antibodies or antibody fragments of the present invention are useful for immunoassays which detect or quantitate HER2 or cells bearing HER2 in a sample. Such an immunoassay typically comprises incubating a biological sample from a subject with a need therefor in the presence of a detectably labeled antibody of the present invention capable of identifying the tumor antigen, and detecting the labeled antibody which is bound in a sample.

In an aspect of the present invention the level, localization of one or more forms of HER2, including HER2, can determine, confirm or indicate the status of a cell, collection of cells, sample from a subject in need thereof. As used herein, "confirm" means that based on the level, localization or both of one or more forms of HER2, including HER2, in a cell, collection of cells or sample, subject etc provides a sufficient basis to characterize the status of a cell, collection of cells, sample or subject etc. As used herein, "confirm" means that based on the level, localization or both of one or more forms of HER2, including HER2, in a cell, collection of cells or sample, subject etc provides in combination with other analysis a basis to characterize the status of a cell, collection of cells, sample or subject etc. As used herein, "indicate" means that based on the level, localization or both of one or more forms of HER2, including HER2, in a cell, collection of cells or sample, subject etc provides that more likely than not or greater probability of determining the status of a cell, collection of cells, sample or subject etc. is of a particular status.

In one aspect of the present invention, the observation of HER2 distribution can be used to detect the stages associated with a particular disease, for example, breast cancer. The tissue specimens can be incubated with HER2 antibody, and the resultant HER2 antigen-HER2 antibody complex can be detected using standard immunohistochemical staining.

In another aspect of the present invention, immunohistochemical staining of HER2 antigen-HER2 antibody complex can indicate different stages of breast cancer in breast tissue.

In one aspect, the HER2 antibody can be used to detect various stages of breast cancer.

In another aspect of the present invention, immunohistochemical staining of HER2 antigen-HER2 antibody complex may be used to detect breast cancer in tissue specimens collected from breast cancer patients. In one aspect, detection of breast cancer in tissue specimens comprises: (a) obtaining said tissue specimen, (b) contacting said tissue specimen with an antibody capable of preferentially detecting a soluble form of HER2 antigen, and (c) staining said tissue specimen with an immunohistochemical staining. In one aspect of the invention, the staining indicates the presence of breast cancer in said tissue specimen.

In one aspect, a status of a cell or collection of cells can be determined using an antibody of the present invention or of fragment thereof whether that cell, collection of cells, sample etc. are metastatic tumor cells, non-metastatic tumor cells, from a solid tumor or normal cells. A status of a subject can include whether the analysis provides information on whether a metastatic cancer or non-metastatic tumor is present in the subject.

Examples of confirmatory analysis, assays, tests, such as histological examination of samples, and so forth that can be used to confirm or in combination with those disclosed herein include, without limitation, those set forth in Alper, US Publication No. 2008/0293162.

In an aspect of the present invention the level, localization or both of one or more forms of HER2, including HER2, is diagnostic or prognostic of a disease or outcome probability.

In an aspect of the present invention a reduced level of HER2 antigen of a present invention in blood, collection of cells or sample can diagnose, prognose, determine, confirm or indicate that such derived is from a metastatic tissue. In one aspect, "reduced" can mean reduced relative to a control, with the control being a normal cell of the same type that is non-metastatic. In this aspect, the reduction can be greater than 10, 20, 30, 40, 50, 60, 70, 80, 90, 95, or 99%.

In an aspect of the present invention, a similar level of HER2 antigen of a present invention in blood, collection of cells or sample to a normal control can diagnose, prognose, determine, confirm or indicate that such cell was derived from a non-metastatic tissue.

In an aspect of the present invention, a lack of localization of HER2 in a cell nucleus can diagnose, prognose, determine, confirm or indicate that such derived is from a metastatic tissue.

In an aspect of the present invention, localization of HER2 in a cell, collection of cells or sample to a normal control can diagnose, prognose, determine, confirm or indicate that such derived from a non-metastatic tissue.

In an aspect of the present invention, the cell, collection of cells or sample is a cervical or breast cell collection of cells or sample, in particular human breast cells.

Antibodies and antibody fragments of the present invention are also useful for immunopathological analysis, such as the differential diagnosis of tumor type, and the subclassification of the tumor based on its expression or localization of at least one form of HER2, including HER2, including, without limitation, assessment of metastatic potential, predicted responses to therapy, and overall prognosis.

HER2 antibodies and antibody fragments permit the definition of subpopulations of tumor cells among the heterogeneous cells present in a growing tumor and can be used, for example, in the typing and cross-matching of the tumor cell "lines," including, without limitation, by means of flow cytometry, both at the time of surgery and prior to therapy. An analysis of the tumor cell populations or subpopulations with antibodies or antibody fragments of this invention, and a battery of additional antibodies or antibody fragments, can be used to define (a) which antigen preparation would be the most appropriate for specific active immunotherapy, (b) which antibody or antibody fragment or chimeric antibody would be efficacious for the particular cancer; and (c) which antibody or combination of antibodies or antibody fragments should be used for imaging the patient at a later date in search for recurrent or metastatic tumors.

A biological sample can be treated with nitrocellulose, or other solid support or carrier which is capable of immobilizing cells, cell particles or soluble proteins or glycoproteins. The support can then be washed with suitable buffers followed by treatment with the detectably labeled antibody of the present invention. The solid phase support can then be washed with the buffer a second time to remove unbound antibody. The amount of bound label on the solid support can then be detected by conventional means.

One of the ways in which the antibody of the present invention can be detectably labeled is by linking the same to an enzyme and use in an enzyme immunoassay (EIA) or enzyme-linked immunosorbent assay (ELISA). This enzyme, when subsequently exposed to its substrate, will react with the substrate generating a chemical moiety which can be detected, for example, by spectrophotometric, fluorometric or by visual means. In an alternate embodiment, the enzyme is used to label a binding partner for the antibody of the invention. Such a binding partner can be an antibody against the constant or variable region of the antibody of the invention, such as a heterologous anti-mouse immunoglobulin antibody. Alternatively, the binding partner can be a non-antibody protein capable of binding to the antibody of the present invention.

By radioactively labeling the antibodies of the present invention, it is possible to detect HER2 through the use of a radioimmunoassay (RIA). The radioactive isotope can be detected by such means as the use of a gamma counter or a scintillation counter or by autoradiography. Isotopes which are particularly useful for the purpose of the present invention are known in the art.

It is also possible to label the antibodies of the present invention with a fluorescent compound. When the fluorescently labeled antibody is exposed to light of the proper wave length, its presence can then be detected due to fluorescence. The antibodies of the present invention also can be detectably labeled by coupling to a chemiluminescent compound. The presence of the chemiluminescently labeled antibody is then determined by detecting the presence of luminescence that arises during the course of a chemical reaction. A bioluminescent compound can also be used to label the antibodies of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and sequorin.

Detection of the antibody, fragment or derivative can be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection can also be accomplished by visual comparison of the extent of enzymatic reaction of a substrate in comparison with similarly prepared standards.

In situ detection can be accomplished by removing a specimen from a patient, and providing the labeled antibody, or the unlabelled antibody plus a labeled binding partner to such a specimen. Through the use of such a procedure, it is possible to determine not only the presence of the antigen but also its distribution in the examined tissue. Using the present invention, those of ordinary skill will readily perceive that any of a wide variety of histological methods (such as staining procedures) can be modified in order to achieve such in situ detection. Such methods include, for example, immunohistochemical staining procedures. In an aspect, an avidin-biotin immunoperoxidase staining system can be used, and a kit utilizing this system is also contemplated, although the methods of the present invention can utilize any suitable staining procedures known in the art.

Kits according to the present invention can include frozen or lyophilized antibodies to be reconstituted by thawing or by suspension in a liquid vehicle. The kits can also include a carrier or buffer. Preferably, the kit also comprises instructions for reconstituting and using the antibody. The kit employing antibodies, including chimeric and humanized antibodies of the present invention, can be used for immunohistochemical evaluation of cancers, including cancer of the breast, ovary, cervix, prostate, colon, stomach, kidney, liver, head, neck, lung, blood, pancreas, skin, testicle, thyroid and brain, most preferentially human breast, ovary, head, neck, and brain, in particular human breast cells.

The kits including the reagents necessary for immunohistochemical analysis can be provided as follows: (a) HER2 antibody or antibody fragment of the present invention, or chimeric or humanized variants thereof; (b) blocking reagent (in the form of, for example, goat serum) and secondary antibody (such as, for example, goat anti-mouse antibody); (c) detectable marker (such as, for example, immunoperoxidase or alkaline phosphatase); and (d) developing reagents. The primary antibody (HER2 antibody or antibody fragment or variants thereof) serves as an antigen which can bind more than one secondary antibody. The secondary antibodies form a "bridge" between the primary antibody and the complex formed by the detectable marker and developing reagent (for example, a horseradish peroxidase-antiperoxidase complex).

Any suitable detection system can be used in accordance with the methods and kits of the present invention. Such detection systems are widely used in immunofluorescence applications, and can be imaged using techniques including, but not limited to, flow cytometry, microscopy, Western blotting, and ELISAs. Suitable detection systems can employ conjugates of secondary antibodies, conjugates of colloidal gold, or conjugates of secondary proteins, in order to amplify the signal from a primary protein (in the context of the present invention, the primary protein signal being amplified is bound a HER2 antibody, which can or cannot be labeled, for example with a protein such as biotin), which is in turn being used to detect a specific target (in the context of the present invention, the target is a HER2 expression product).

Suitable secondary conjugates for use in the methods and kits of the present invention can include, but are not limited to, enzyme conjugates of a secondary antibody and an enzyme such as horseradish peroxidase or alkaline phosphatase; enzyme conjugates of avidin or streptavidin and an enzyme such as horseradish peroxidase or alkaline phosphatase; enzyme conjugates of protein A or protein G and an enzyme such as horseradish peroxidase or alkaline phosphatase; conjugates of colloidal gold and a secondary antibody; conjugates of colloidal gold and avidin or streptavidin; conjugates of magnetic particles and a secondary antibody; and conjugates of secondary antibodies and labels such as fluorescent dyes and biotin. The present invention is not limited to any particular detection systems, and it is considered within the ability of the person of ordinary skill in the art to utilize these or other detection systems in accordance with the present invention. These secondary conjugates (also referred to as labels in the context of the present invention) are useful for visualizing antigen-antibody complexes.

The antibody or antibody fragment of the present invention can also be adapted for utilization in an immunometric assay, also known as a "two-site" or "sandwich" assay. In a typical immunometric assay, a quantity of unlabelled antibody (or fragment of antibody), is bound to a solid support that is insoluble in the fluid being tested and a quantity of detectably labeled soluble antibody is added to permit detection and/or quantitation of the ternary complex formed between solid-phase antibody, antigen, and labeled antibody.

For purposes of in vivo imaging of breast, ovary, cervix, prostate, colon, stomach, kidney, liver, head, neck, lung, blood, pancreas, skin, testicle, thyroid and brain, most preferentially human breast, ovary, head, neck, and brain, in particular human breast cancer and other cancers using the antibodies or antibody fragments of the present invention, there are many different labels and methods of labeling known to those of ordinary skill in the art. Examples of the types of labels which can be used in the present invention include radioactive isotopes, paramagnetic isotopes, and compounds which can be imaged by positron emission tomography (PET).

6. Pharmaceutical Compositions and Methods of Treatment

Another aspect of the invention provides a composition comprising any of these antibodies, optionally in combination with a pharmaceutically acceptable carrier. In another aspect, an antibody of the present invention is optionally in combination with one or more active agents, drugs or hormones.

The present invention also provides a method of treating human or animal subjects suffering from or at risk of a cancer that expresses HER2, such as solid tumors of the breast, ovary, cervix, prostate, colon, stomach, kidney, liver, head, neck, lung, blood, pancreas, skin, testicle, thyroid and brain, most preferentially human breast, ovary, head, neck, and brain, in particular human breast cells, the method comprising administering to the subject a therapeutically effective amount of an antibody of the present invention, or a pharmaceutical composition comprising a therapeutically effective amount of an antibody of the present invention.

The term "subject" as used herein refers to any subject in need of treatment, preferably a human patient or subject.

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs, or primates. The animal model can also be used to determine the appropriate concentration range and route of administration. Such information can then be used to determine useful doses and routes for administration in humans.

An effective amount for a human subject can depend upon the severity of the disease state, the general health of the subject, the age, weight and gender of the subject, diet, time and frequency of administration, drug combination(s), reaction sensitivities and tolerance/response to therapy and can be determined by routine experimentation and is within the judgment of the clinician. Generally, an effective dose will be from 0.01 mg/kg to 50 mg/kg, preferably 0.1 mg/kg to 20 mg/kg, more preferably from about 1 mg/kg to about 15 mg/kg.

Compositions can be administered individually to a patient or can be administered in combination with other agents, drugs or hormones. According to some aspects, antibodies can be conjugated with these agents. A summary of the ways in which the antibodies of the present invention can be used therapeutically includes direct cytotoxicity by the antibody, either mediated by complement or by effector cells, or conjugated to anti-tumor drugs, toxins, and radionuclides. Antibodies can also be used for ex vivo removal of tumor cells from the circulation or from bone marrow.

Cytotoxic proteins can include, but are not limited to, Ricin-A, *Pseudomonas* toxin, Diphtheria toxin, and tumor necrosis factor. Diagnostic radionuclides and cytotoxic agents such as cytotoxic radionuclides, drug and proteins can also be conjugated to the antibodies of the present invention. Examples of radionuclides which can be coupled to antibodies and selectively delivered in vivo to sites of antigen include $^{212}Bi$, $^{131}I$, $^{186}Re$, and $^{90}Y$, among others. Radionuclides can exert their cytotoxic effect by locally irradiating the cells, leading to various intracellular lesions, as is known in the art of radiotherapy. Examples of cytotoxic drugs which can be conjugated to antibodies and subsequently used for in vivo therapy include, but are not limited to, daunorubicin, doxorubicin, methotrexate, and Mitomycin C. Cytotoxic drugs can interface with critical cellular processes including DNA, RNA, and protein synthesis.

A dose at which the antibody molecule of the present invention is administered depends on the nature of the condition to be treated, and on whether the antibody molecule is being used prophylactically or to treat an existing condition. If administered prophylactically, i.e., as a vaccine, the antibody is administered in an amount effective to elicit an immune response in the subject.

If the antibody molecule has a short half-life (e.g. 2 to 10 hours) it can be necessary to give one or more doses per day. Alternatively, if the antibody molecule has a long half life (e.g. 2 to 15 days) it can only be necessary to give a dosage once per day, per week or even once every 1 or 2 months.

A pharmaceutical composition can also contain a pharmaceutically acceptable carrier for administration of the antibody. The carrier should not itself induce the production of antibodies harmful to the individual receiving the composition and should not be toxic. Suitable carriers include those known in the art, and can be selected from large, slowly metabolized macromolecules such as proteins, polypeptides, liposomes, polysaccharides, polylactic acids, polyglycolic acids, polymeric amino acids, amino acid copolymers and inactive virus particles, although suitable carriers are not limited to these examples.

Preferred forms for administration include forms suitable for parenteral administration, e.g. by injection or infusion, for example by bolus injection or continuous infusion. Where the product is for injection or infusion, it can take the form of a suspension, solution or emulsion in an oily or aqueous vehicle and it can contain formulatory agents, such as suspending, preservative, stabilizing and/or dispersing agents. Alternatively, the antibody molecule can be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

A pharmaceutical compositions of this invention can be administered by any number of routes including, but not limited to, oral, intravenous, intramuscular, intra-arterial, intramedullary, intrathecal, intraventricular, transdermal, transcutaneous, subcutaneous, intraperitoneal, intranasal, enteral, topical, sublingual, intravaginal or rectal routes. Hyposprays can also be used to administer the pharmaceutical compositions of the invention. Therapeutic compositions can be prepared as injectables, either as liquid solutions or suspensions. Solid forms suitable for solution in, or suspension in, liquid vehicles prior to injection can also be prepared.

Direct delivery of the compositions will generally be accomplished by injection, subcutaneously, intraperitoneally, intravenously or intramuscularly, or delivered to the interstitial space of a tissue. Dosage treatment can be a single dose schedule or a multiple dose schedule.

When an antibody or antibody fragment composition is to be administered by a route using the gastrointestinal tract, the composition can to contain additional agents which protect the antibody from degradation but which release the antibody once it has been absorbed from the gastrointestinal tract. Such additional agents are well-known to those skilled in the art.

Antibodies of the present invention can also be administered in methods of conducting gene therapy. In order to achieve this, DNA sequences encoding the heavy and light chains of the antibody molecule under the control of appropriate DNA components are introduced into a patient such that the antibody chains are expressed from the DNA sequences and assembled in situ.

7. HER2Expression Products as Drug Development Targets

In addition, the present invention relates to the discovery that HER2 and homologues thereof can cause the expression or change in subcellular localization of HER2 antigens by cells in patients suffering from various diseases, such as cancers, and more specifically solid tumors of the breast, ovary, cervix, prostate, colon, stomach, gastrointestinal tract, kidney, liver, head, neck, lung, blood, pancreas, skin, testicle, thyroid and brain, most preferentially human breast, ovary, head, neck, and brain, in particular human breast cells. Cell lines that may be used in the methods of the present invention include, but are not limited to, SK-BR3, BT474, MCF7, MDA-MB-231, MDA-MB-175, MDA-MB-453, MDA-MB-361, Calu3 and SKOV3 cells. Expression of HER2 antigens presents a novel drug development target, and accordingly the present invention also relates to the use of such HER2 antigens as biomarkers that can be targeted not only by the HER2 antibodies or antibody fragments of the present invention, but also by various other molecules, such as siRNA, antisense oligonucleotides, vaccines, and chemical compounds.

Methods for developing drugs useful in treating and/or diagnosing diseases characterized by the expression of gene products of HER2 and homologues thereof can include the steps of identifying the gene products expressed by HER2 and homologues thereof in a subject having a disease, and utilizing those gene products as to development and identify drugs that specifically target the gene products.

Once candidate drugs have been developed based on the HER2 antigens, the HER2 antigens and HER2 antibodies and antibody fragments of the present invention can be used to aid in screening the various drug candidates, in order to identify those drug candidates that exhibit a desired level of specificity for diseased cells presenting HER2 expression products.

The following examples are non-limiting illustrative examples.

Example 1

Alper-HER2 mAb 2HE Molecular Weight

Approximately 1 ug of a purified mAb (identified as HER2MoAb 2HE) is suspended in PBS, and is applied under reducing (boiled 3 minutes in sample buffer with beta-mercaptoethanol and 10% SDS) to 10% Bis-Tris gels and run at 120 volts. The gels are then stained with Coomassie Blue (0.1% (w/v) Coomassie blue R350, 20% (v/v) methanol, and 10% (v/v) acetic acid), destained in 50% (v/v) methanol in water with 10% (v/v) acetic acid, and images of such gels are taken. Under denatured conditions, the heavy chain of IgG1 Ab clone name, Alper-HER2 mAb 2HE is detected at ~50 kDa and light chain of IgG1 Ab clone name, Alper-HER2 mAb 2HE is detected at ~25 kDa.

Example 2

A 185 kDa MWt Protein is Detected from SK-BR3 Culture Supernatant

A 185 kDa MWt protein is detected from SK-BR3 culture supernatant when blotted with Alper-HER2 mAb 2HE. Proteins (500 μg/ml) from the breast carcinoma cell line (SK-BR3) and purified recombinant protein of Homo sapiens v-erb-b2 erythroblastic leukemia viral oncogene homolog 2 [neuro/glioblastoma derived oncogene homology (avian) (ERBB2), transcript variant 1] (From Origene Technologies Incorporation) are resolved by SDS-PAGE on 8% polyacrylamide gel and transferred to PVDF. The membranes were blocked by 5% milk/PBST buffer and incubated with Alper-HER2 mAb 2HE at a concentration of 5 μg/ml overnight at 4° C. in a 5% milk/PBST buffer. After washing, the membranes are incubated with a HRP-conjugated sheep anti-mouse IgG antibody at a 1:3000 dilution. Bands are detected with an ECL kit and Kodak BioMax™ film.

Example 3

Subcellular Localization of HER2

Human normal mammary epithelial cells, (HMEC), non-metastatic breast cancer cells (SKBR3) and metastatic breast cancer cells (MDA-MB-231) are fixed with 10% paraformaldehyde, permeabilized with 0.1% Triton-X100™. HER2 expression was then visualized with an anti-HER2 mAb (mAb clone name: Alper-HER2 mAb 2HE) and secondary FITC-labeled anti-mouse antibodies (Jackson ImmunoResearch, West Grove, Pa.). Images are analyzed using an Olympus microscope equipped with 20× and 10× objective lens. Staining is subcellularly localized to the plasma membrane in HMEC and SKBR3 cells. Staining is localized intracellularly in MDA-MB-231 cells, mostly to the ruffles in the membranes.

Example 4

HER2 is the Antigen for the Alper-HER2 mAb 2HE

An antigen for Alper-HER2 mAb 2HE is isolated as Spot 1 on a 2D gel. Coomassie Brilliant Blue R-250 stained PVDF membrane is blocked for two hours in 5% nonfat dry milk (NFDM) in Tween-20 tris buffer saline (TTBS) and rinsed in TTBS. A blot is incubated in primary antibody (Alper-HER2 mAb 2HE diluted 1:200 in 2% NFDM TTBS) overnight. A blot is rinsed 3×10 minutes in TTBS, placed in secondary antibody (anti-mouse IgG-HRP [GE Healthcare, Cat #NA931V, Lot #397188], 1:2,000 diluted in 2% NFDM TTBS) for two hours, rinsed 3×10 minutes in TTBS, treated with ECL, and exposed to x-ray film. Spot 1 is digested with trypsin and analyzed by MALDI-MS. A major protein identified is HER2. Also present, probably as contaminants, are albumin (fragment) and hemoglobin alpha and beta.

Example 5

An Alper-HER2 mAb 2HE Epitope

Alper-HER2 mAb 2HE recognizes a phosphorylated native conformation of a HER2 extracellular domain. See SEQ ID NOs: 10-18. The HER2 gene encodes a 185 kDa transmembrane glycoprotein that consists of a 620 aa extracellular domain, followed by a 23 aa transmembrane domain and a 490 aa intracellular domain with a tyrosine kinase activity. SKBR3 cells ($1 \times 10^6$) are cultured in 100 mm culture dishes and are washed with PBS and lysed in buffer 10 (1× Lysis buffer: 10 mM Tris, pH8.0, 130 mM NaCl, 1% Triton X-100, 10 mM NaF, 10 mM NaPi, 10 mM NaPPi). Cell lysates (250 mg protein/ml) are immunoprecipitated with the following mouse MAbs specific to HER2 (Alper-HER2 mAb 2HE), and phosphotyrosine (PY-20, Transduction Laboratories) at 4° C. overnight. All antibodies are used at concentrations suggested by the manufacturers.

Immunoprecipitates are further incubated with protein A-Sepharose™ at 4° C. for 2 hr. Proteins that bind to protein G-Sepharose™ are recovered by centrifugation, released by heating, resolved by two 6-8% SDS-PAGE gels, and the two gels are transferred to nitrocellulose sheets for western blot analysis. For HER2 protein detection, one of the blots is first blocked with 5% dry milk in Phosphate-buffered saline with Tween-20TH for 1 hr at 20° C. and then incubated with Alper-HER2 mAb 2HE. Bound mouse antibodies are detected using sheep anti-mouse IgG conjugated to horseradish peroxidase for 1 hr at 20° C. Immunoreactive bands are detected by the enhanced chemiluminescence (ECL) reaction (Amersham). Bands are measured by densitometric analysis.

For tyrosine kinase phosphorylation analysis, another blot is first blocked with 5% dry milk in Phosphate-buffered saline with Tween-20 for 1 hr at 20° C. and then incubated with PY-20 moab specific to phosphotyrosine. Bound mouse antibodies are detected using sheep anti-mouse IgG conjugated to horseradish peroxidase for 1 hr at 20° C. Immunoreactive bands are detected by the enhanced chemiluminescence (ECL) reaction (Amersham). Bands are measured by densitometric analysis.

A band with a molecular weight of 185 kDa is observed when SKBR3 cells are immunoprecipitated with Alper-HER2 mAb 2HE and blotted with anti-phosphotyrosine moab in one blot. A similar band with a molecular weight of 185 kDa is also observed when SKBR3 cells are immunoprecipitated with anti-phosphotyrosine moab and blotted with Alper-HER2 moab in the other blot. Alper-HER2 mAb 2HE recognizes the phosphorylated form of HER2.

Example 6

Breast Cancer Patients Demonstrate Higher Soluble/Shed HER2 Levels than Control Groups Plasma samples are obtained from control and breast cancer patient groups and are diluted with PBS at a ratio of 1:100. Plasma HER2 levels are measured with a competitive (one-step) enzyme-linked immunosorbent enzyme assay (ELISA). The polysorp ELISA plates (Nalgene NUNC® International, Rochester, N.Y.) are coated with 100 μl/well of diluted plasma and incubated at 4° C. overnight. Wells are washed with PBS and incubated at room temperature for one hour with blocking buffer (5% BSA in PBS). After washing with PBS, the primary antibody, Alper-HER2 mAb 2HE is added in dilution buffer (45 μg/ml) (PBS buffer, 1% BSA, 0.01% Tween-20). The wells are washed with PBS/0.03% Tween-20 and incubated at room temperature for one hour with 100 μl/well secondary antibody (HRP-Donkey anti-mouse IgG, Jackson ImmunoResearch, West Grove, Pa.) diluted 1:3000. After washing the wells, 100 μl Immunopure™ TMB substrate solution (Pierce, Rockford, 1L) is added. Color reaction is stopped by the addition of 100 μl/well 1N $H_2SO_4$ and the analysis is performed with an ELISA Reader. The figures represent optical density (OD) values of plasma readings for HER2 levels. The blood plasma samples are analyzed in a blinded fashion. Data are representative of three independent experiments performed in triplicate.

There is a significant difference in the plasma levels of HER2 detected between control (n=5) and breast cancer (non-metastatic and metastatic) groups (n=15) using Alper-HER2 mAb 2HE (T-Test showed p<0.001 between control and cancer plasma samples). Alper-HER2 mAb 2HE detects HER2 in plasma at levels as low as 5 ng/ml. This detection threshold is better than that reported for current FDA approved HER2 blood tests. See, for example, Immunoassay 510(k) Summary of Safety and Effectiveness for the ADVIA Centaur® HER-2/neu System. The affinity of Alper-HER2 mAb 2HE for this antigen is better than commercial antibodies.

Example 7

Alper-HER2 mAb 2HE Heavy Chain Antibody Sequence

Alper-HER2 mAb 2HE heavy chain antibody sequence is determined by first extracting total cellular RNA from Her2-specific hybridoma cells using Qiagen Mini RNeasy kit (Qiagen Inc., Valencia, Calif., USA) following the kit instructions. The RNA is reverse-transcribed into complementary DNA (cDNA) using SuperScript® III First-Strand Synthesis System (Invitrogen, Carlsbad, Calif., USA). 1 μg of cDNAs from each sample were subjected PCR on MJ Mini Gradient Thermal Cycler™ (Bio-Rad, Foster, Calif., USA). The mouse universal Ig heavy-chain primers are used to amplify the V-region cDNA; the primer sequences for heavy chain are VH 5'-tgaggtgcagctggaggagtc-3' (SEQ ID NO: 19) and JH 5'-gt-gaccgtggtcccttggccccag-3' (SEQ ID NO: 20). The PCR cycles for amplification are conducted at the initial 6 cycle of 94° C. for 15 seconds, 62° C. (−1.2° C./cycle) for 30 seconds and 72° C. for 30 seconds, and then following 30 cycles of 94° C. for 15 seconds, 56° C. for 30 seconds and 72° C. for 30 seconds. Amplification achieves a single band at ~380 bp when running on 1% agarose gel. PCR products are purified and inserted into a plasmid vector (pCR4-TOPO™, Invitrogen, Carlsbad, Calif., USA) following manufacturer's instruction. Four single colonies are taken for each chain, cultured and sub-cloned if need. The plasmids from each colony are isolated using Qiagen QIAprep™ Spin Miniprep Kit (Qiagen Inc). The PCR inserts are verified by restriction analysis and then the plasmids are used for sequencing (Macrogen, Rockville, Md., USA).

For sequence analysis and CDR determination the sequences from a forward and reverse primer and from each colony are aligned and checked carefully to compare their consistency, which combined with sequencing spectra checking. The sequences from cDNAs are identified using the Abysis™ database, which integrates sequence data from Kabat, IMGT and the PDB with structural data from the PDB. See Dr. Andrew C. R. Martin's book chapter *Protein Sequence and Structure Analysis of Antibody Variable Domains*. In: *Antibody Engineering Lab Manual* (Ed.: Duebel, S, and Kontermann, R., Springer-Verlag, Heidelberg, ISBN-13: 978-3540413547, also available on the world wide web at bioinf.org.uk/abs).

The sequences of the FWRs and CDRs of the heavy chain of the HER2 mAb 2HE are shown in FIG. 2 and SEQ ID NOs: 1-4 and 8. Amino acid residues in the polypeptide sequence provided below the polynucleotide sequence in FIG. 2 are numbered using the convention of Kabat et al. The bold residues in FIG. 2 set forth in underlined text indicate specificity determining residues (SDRs).

Example 8

Alper-HER2 mAb 2HE Light Chain Antibody Sequence

Alper-HER2 mAb 2HE light chain antibody sequence is determined by first extracting total cellular RNA from Her2-specific hybridoma cells using Qiagen Mini RNeasy Kit™ (Qiagen Inc., Valencia, Calif., USA) following the kit instructions. The RNA is reverse-transcribed into complementary DNA (cDNA) using SuperScript® III First-Strand Synthesis System (Invitrogen, Carlsbad, Calif., USA). 1 μg of cDNAs from each sample were subjected PCR on MJ Mini Gradient Thermal Cycler™ (Bio-Rad, Foster, Calif., USA). The mouse universal Ig light chain primers are used to amplify the V-region cDNA; the sequences for light chain are VK 5'-gacattctgatgacccagtct-3' (SEQ ID NO: 21) and JK 5'-ttttatttccagcttggtccc-3' (SEQ ID NO: 22). The PCR cycles for amplification are conducted at the initial 6 cycle of 94° C. for 15 seconds, 62° C. (−1.2° C./cycle) for 30 seconds and 72° C. for 30 seconds, and then following 30 cycles of 94° C. for 15 seconds, 56° C. for 30 seconds and 72° C. for 30 seconds. Amplification achieves a single band at ~380 bp when running on 1% agarose gel. PCR products are purified and inserted into a plasmid vector (pCR4-TOPO™, Invitrogen, Carlsbad, Calif., USA) following manufacturer's instruction. Four single colonies are taken for each chain, cultured and sub-cloned if need. The plasmids from each colony are isolated using Qiagen QIAprep Spin Miniprep Kit™ (Qiagen Inc). The PCR inserts are verified by restriction analysis and then the plasmids are used for sequencing (Macrogen, Rockville, Md., USA).

For sequence analysis and CDR determination, the sequences from a forward and reverse primer and from each colony are aligned and checked carefully to compare their consistency, which combined with sequencing spectra checking. The sequences from cDNAs are identified using the Abysis™ database, which integrates sequence data from Kabat, IMGT and the PDB with structural data from the PDB. See Dr. Andrew C. R. Martin's book chapter *Protein Sequence and Structure Analysis of Antibody Variable Domains*. In: *Antibody Engineering Lab Manual* (Ed.: Duebel, S, and Kontermann, R., Springer-Verlag, Heidelberg, ISBN-13: 978-3540413547, also available on the world wide web at bioinf.org.uk/abs). FWRs and CDRs of the light chain of the HER2 mAb, Alper-HER2 mAb 2HE, are provided in FIG. 3. See FIG. 3 and SEQ ID NOs: 5-7 and 9.

Example 9

Detection of HER2 in Fomalin-Fixed, Paraffin Embedded (FFPE) Tissue Sections

An Alper BioTech, LLC HER-2 IHC Kit is a sensitive immunohistochemistry kit that is specific for the detection of HER-2 protein in formalin fixed, paraffin-embedded (FFPE) tissue sections. Alper Anti-HER-2 monoclonal antibody 2HE recognizes a N-terminus of the native form of HER-2.

The protocol written here is optimized for specific HER-2 protein staining and developed using a breast cancer tissue microarray and process guidelines provided by The Yale Pathology/Yale Cancer Center Tissue Microarray Facility. This protocol is directed toward the staining of tissues that have been fixed (usually in neutral buffered formalin) and subsequently embedded in paraffin before sectioning.

Immunohistochemical staining is performed as follows. Incomplete removal of paraffin can cause poor staining of the section. Accordingly, prior to staining, FFPE samples are deparaffinized and rehydrated as follows. Immerse slides in xylene and incubate for 2×15 minutes; immerse slides in xylene:ethanol (1:1) for 5 minutes; immerse slides in 100% ethanol for 5 minutes, and follow with 95%, 75% and 50% ethanol for 3 minutes each; rinse slides with reagent-quality water for 5 minutes and keep in water until ready to perform antigen retrieval.

Following deparaffinization and rehydration, antigen is retrieved using heat induced antigen retrieval (HIAR) as follows. Fill plastic Coplin Jar/container with Retrieval Buffer; place the Coplin jar/container in steamer; turn on steamer and preheat to 90-100° C. Carefully put slides into the Coplin jar/container and steam for 40 min (95-100° C.); turn off the steamer; remove the Coplin jar/container to room temperature and allow the slides to cool for 20 min. Rinse slides with Wash Buffer for 3×3 minutes and begin staining procedure.

The retrieved antigen is stained for immunohistochemical analysis as follows. Tap off excess Wash buffer; apply sufficient Peroxidase Blocking Buffer to cover specimen, and incubate for 5 minutes; rinse sections with Washing Buffer for 3×3 minutes; tap off excess buffer. Apply sufficient Background Block to cover specimen and incubate for 5 minutes; rinse sections with Washing Buffer for 3×3 minutes; tap off excess buffer. Apply sufficient HER2 antibody (1:300 dilution of 500 µg/mL Alper-HER2 monoclonal antibody 2HE in antibody diluents) to cover specimen, and incubate for 1 hour; rinse sections with Washing Buffer for 5×3 minutes; tap off excess buffer. Apply sufficient Mach3™ polymers (Biocare Medical; Cat No. M3M530 G) to cover specimen, and incubate for 15 minutes; rinse sections with Washing Buffer for 3×3 minutes; tap off excess buffer. Apply sufficient Mach3™ polymers to cover specimen, and incubate for 15 minutes; rinse sections with Washing Buffer for 3×3 minutes; tap off excess Wash Buffer. Apply sufficient diaminobenzedinetetrahydrochlorid (DAB) substrate solution to cover specimen, and incubate until desired stain intensity develops; rinse sections in tap water for 3 minutes; immerse slides in hematoxylin solution, incubate 30 sec to 5 minutes; rinse to clear with tap water and follow by dehydration; immerse slides in 70%, 80%, 95%, 100% ethanol for 2 minutes each, and follow in xylene for 2×2 minutes; dry and mount slides.

Normal, non-metastatic and metastatic breast cancer epithelial cell images are scored from 0 to +3 according to guidelines in HER2 Immunohistochemistry, Tissue Microarray Survey, Her2-A 2010, from the College of American Pathologists (CAP/ASCO Testing guidelines. see also Wolff, A C, et al., *Arch. Pathol. Lab. Med.* (2007) 131:18-43.

Score 0=No staining is observed in invasive tumor cells

Figures 4A, 4B, 4C, 4D:
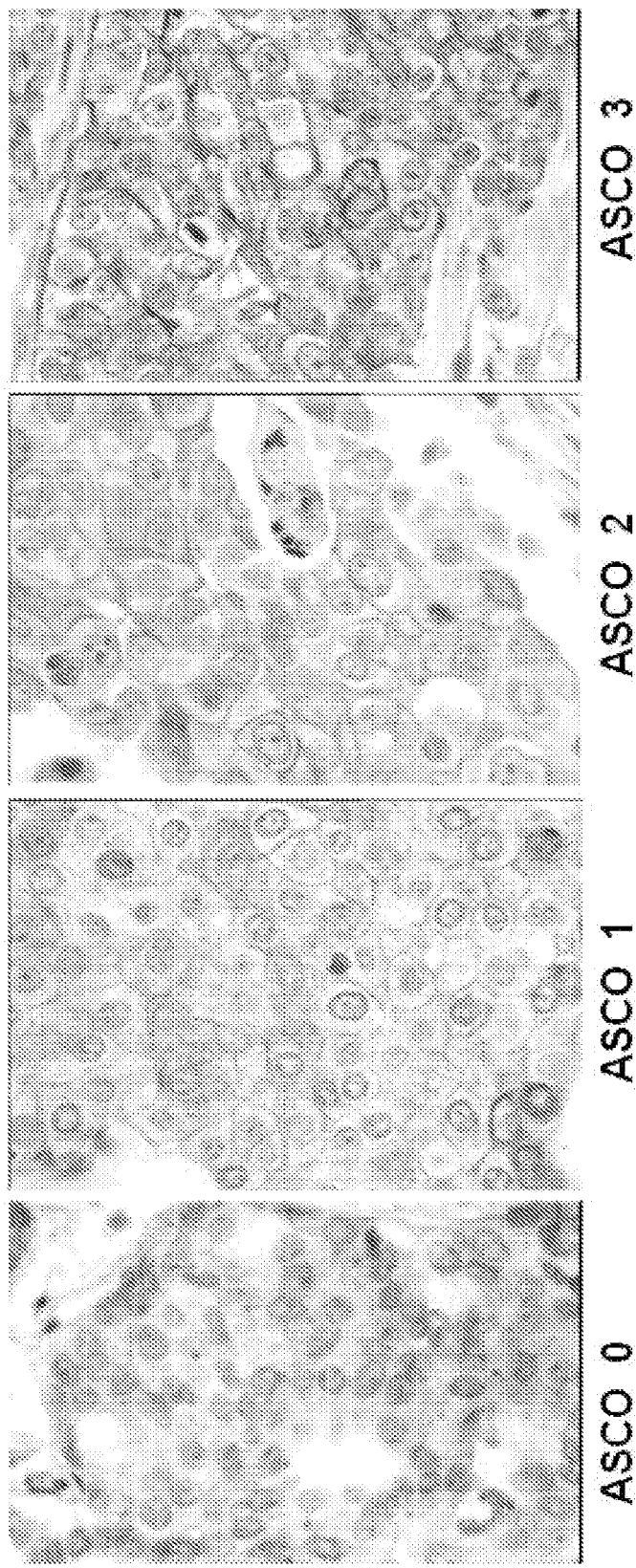
FIGS. 4A, 4B, 4C, and 4D. One normal (score 0) and three breast cancer tissues (scores 1, 2 and 3) stained with Alper-HER2 mAb (2HE).

Score 1+=Weak, incomplete membrane staining in any proportion of invasive tumor cells, or weak, complete membrane staining in less than 10% of cells Score 2+=Complete membrane staining that is non-uniform or weak but with obvious circumferential distribution in at least 10% of cells, or intense complete membrane staining in 30% or less of tumor cells Score 3+=Uniform intense membrane staining of more that 30% of invasive tumor cells Intense staining—easily visualized with 4× or 10× objective Weak staining—visualization requires 40× objective Or if appropriate Insufficient core tissue present No invasive carcinoma present in core The Yale School of Medicine, Department of Pathology, Tissue Microarray and Archiving, YTMA 49(9-10) provides a cohort of 630 tumor patients and 64 healthy controls (714 total). Of the 630 tissue samples from female breast cancer patients (metastatic or nonmetastatic), ~30-50% are found negative for HER2 and designated normal tissues by commercial FDA approved HER2 moabs. These same "negative" samples are identified as HER2 positive breast cancer samples using Alper-HER2 mAb 2HE and methods disclosed above when compared side by side in a blind study. Thus, Alper-HER2 mAb 2HE identifies positive membrane staining in more patients who are scored negative when a commercial HER2 moab is used. Moreover, Alper-HER2 mAb 2HE gives a better result than the commercial HER2 antibodies when an equal concentration of both antibodies is used. See FIG. 4.

TABLE 3

Patient Characteristics for Female Breast Cancer Patients from Yale cohort

| Characteristic | N (%) |
|---|---|
| All | 631 |
| Race | |
| White | 594 (94) |
| Black | 19 (3) |
| Other | 4 (1) |
| Missing | 16 (2) |
| Age | |
| <40 | 47 (7) |
| 40-49 | 123 (19) |
| 50-59 | 170 (27) |
| 60-69 | 159 (25) |

TABLE 3-continued

Patient Characteristics for Female Breast Cancer Patients from Yale cohort

| Characteristic | N (%) |
|---|---|
| ≥70 | 117 (19) |
| Missing | 15 (2) |
| Nuclear Grade | |
| 1 | 106 (17) |
| 2 | 300 (48) |
| 3 | 160 (25) |
| Missing | 65 (10) |
| Nodal Status | |
| Negative | 306 (48) |
| Positive | 311 (50) |
| Missing | 14 (2) |
| ER | |
| 0 | 274 (43) |
| 1 | 70 (11) |
| 2 | 103 (16) |
| 3 | 136 (22) |
| Missing | 48 (8) |
| PR | |
| 0 | 278 (44) |
| 1 | 64 (10) |
| 2 | 98 (16) |
| 3 | 119 (19) |

Example 10

Statistical Correlation between Alper-HER2 mAb 2HE and Estrogen Receptor (ER) in a 700 Breast Cancer Patient Cohort A statistically significant correlation exists between the level of ER staining and Alper-HER2 mAb 2HE staining in a breast cancer cohort of tissue samples from the Yale School of Medicine, Department of Pathology, Tissue Microarray and Archiving, YTMA 49(9-10) (p-value <0.00001). Patient characteristics for female breast cancer patients from Yale cohort are in Table 2. Testing is done at the 0.05 of significance, p-values are 2-sided, Monte-Carlo method was used in estimation of the tests' probabilities. Testing is done using linear by linear association model, a special case of the log linear models used to model ordinal count data in contingency tables. The test statistic for testing independence in this model is the likelihood ratio test statistic (6.975).

TABLE 4

A statistically significant correlation exists between the level of ER staining and Alper-HER2 mAb 2HE

| | Her(0) | Her(1) | Her(2) | Her(3) | total |
|---|---|---|---|---|---|
| ER(0) | 85 | 54 | 43 | 66 | 248.0 |
| ER(1) | 11 | 9 | 16 | 25 | 61.0 |
| ER(2) | 7 | 27 | 23 | 38 | 95.0 |
| ER(3) | 7 | 28 | 25 | 68 | 128.0 |
| | 110.0 | 118.0 | 107.0 | 197.0 | 532.0 |

Example 11

Figure 5:
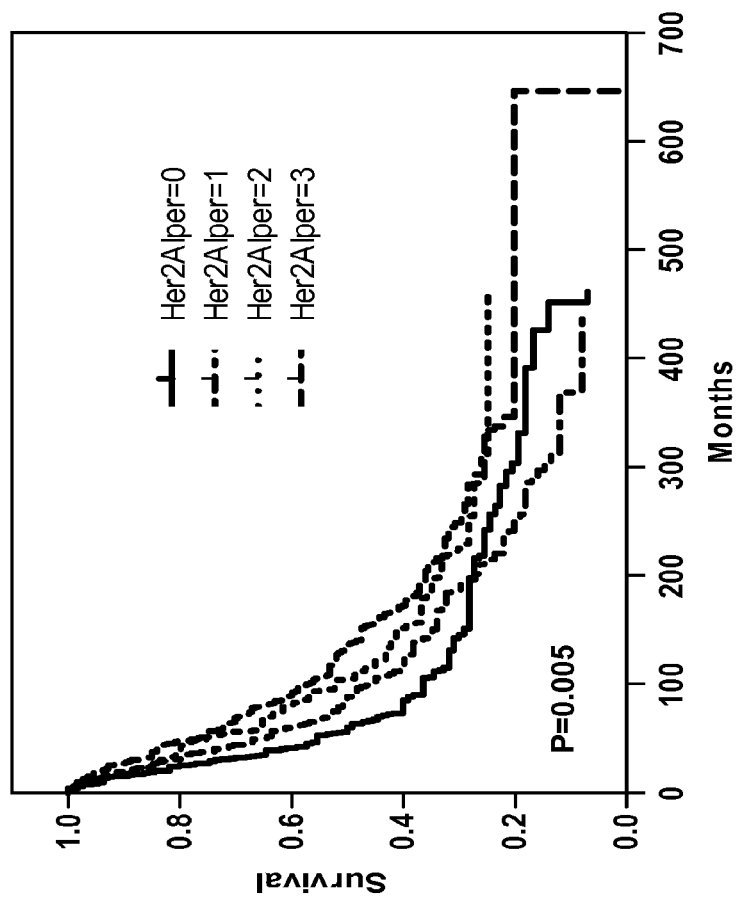
FIG. 5. Overall Survival (OS) functions estimated by the Kaplan-Meier method for breast cancer patients categorized by score with Alper-HER2 mAb (2HE).

Overall Survival (OS) Statistically Significantly Correlated with Level of Alper-HER2 mAb (2HE) Staining in Breast Cancer Patients Overall Survival (OS) functions are estimated by the Kaplan-Meier method and compared to Alper-HER2 mAb (2HE) staining score (0-3). Table 5 lists estimated OS parameters. See also FIG. 5.

TABLE 5

Overall Survival (OS) statistically significantly correlated with level of Alper-HER2 mAb (2HE) staining in breast cancer patients.

| Alper-HER2 mAb (2HE) Score | N = 545 | Median OS, mo | 95% confidence interval (CI), mo |
|---|---|---|---|
| 0 | 112 | 55.8 | 41.4-72.4 |
| 1 | 123 | 79.4 | 60.1-108.3 |
| 2 | 111 | 104.5 | 81.4-138.4 |
| 3 | 199 | 130.7 | 99.0-161.4 |

These four survival functions are different, the log rank test p = 0.005.

Example 12

Increased Overall Survival in Node Positive Patients Correlated with Increased HER2 Expression Using Alper-HER2 mAb (2HE)

Figure 6:
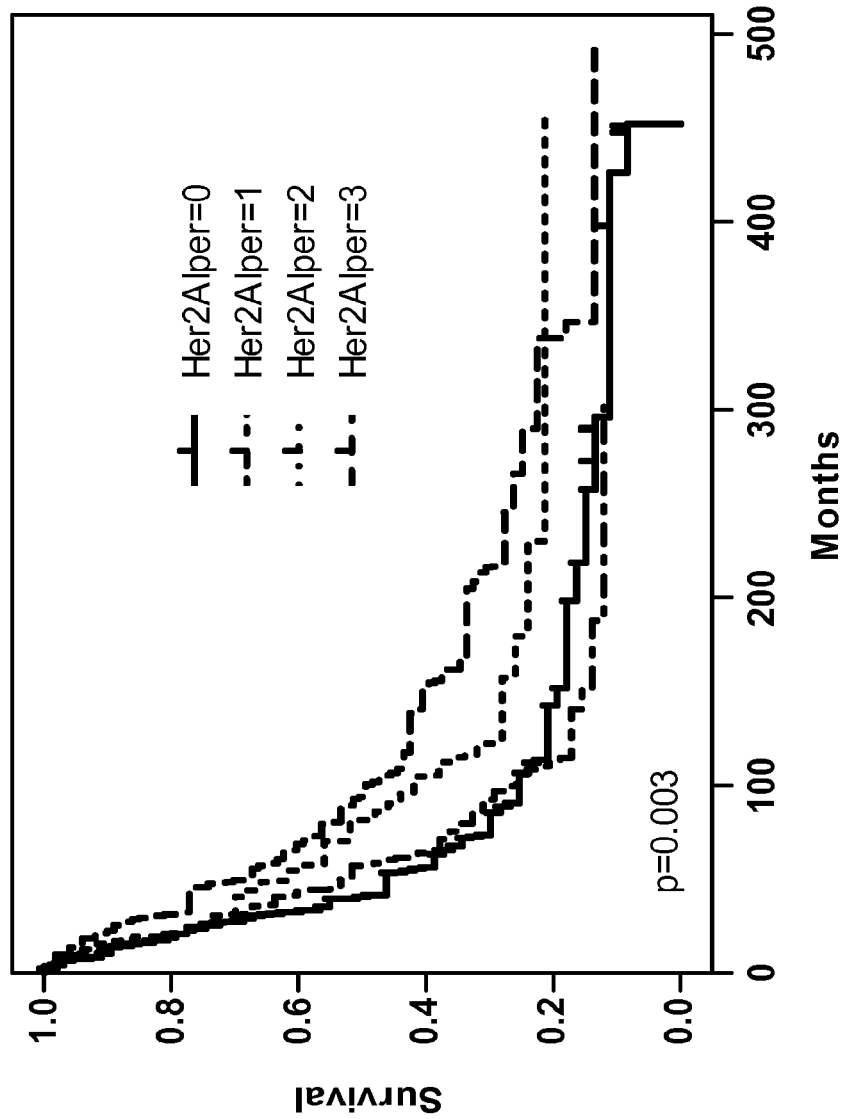
FIG. 6. Overall Survival (OS) functions estimated by the Kaplan-Meier method for breast cancer patients categorized by the score with Alper-HER2 mAb (2HE) in those who were nodal positive.

Overall survival (OS) experience in breast cancer patients who were nodal positive (n=276) is compared to Alper-HER2 mAb (2HE) score using a log rank test. Corresponding survival functions estimated by the Kaplan-Meier method are displayed in FIG. 6. Table 6 lists estimated OS parameters. There was a statistically significant difference in survival experience between these patients, the log rank test p=0.0028. Cancer patients with node-negative or node-positive diseases may have different suggested treatments based on HER-2 status. See Winston, J S, et al., *Am J Clin Pathol* (2004) 121(Suppl 1):S33-S49, hereby incorporated by reference in its entirety. Alper-HER2 mAb (2HE) identifies a subset of node-positive patients with a good prognosis.

TABLE 6

Increased overall survival in node positive patients correlated with increased HER2 expression using Alper-HER2 mAb (2HE).

| Alper-HER2 mAb (2HE) Score | N = 276 | Median OS, mo | 95% confidence interval (CI), mo |
|---|---|---|---|
| 0 | 67 | 40.4 | 31.5-63.4 |
| 1 | 58 | 57.3 | 40.4-71.4 |
| 2 | 50 | 81.4 | 48.5-112.5 |
| 3 | 101 | 93.7 | 68.8-140.4 |

Example 13

FDA-Approved HER2 Immunohistochemistry (1HC) Staining is not Correlated to Overall Survival of Breast Cancer Patients Overall Survival (OS) functions estimated by the Kaplan-Meier method for breast cancer patients was not correlated with the score with Path™ Her2 antibody (Ventana's Pathway-Her2 moab). There is no difference in survival experience between these patients, the log rank test p=0.51. While not limited by mechanism, these two antibodies recognize different HER2 epitopes. The Path™ Her2 moab recognizes an intracellular or carboxyl domain of HER2 protein. Alper-HER2 mAb (2HE) recognizes an extracellular domain (N-terminal).

TABLE 7

FDA-approved HER2 immunohistochemistry (IHC) staining is not correlated to overall survival of breast cancer patients.

| Path Her2 | N = 570 | Median OS, mo | 95% confidence interval (CI), mo |
|---|---|---|---|
| 0 | 357 | 100.3 | 85.5-111.8 |
| 1 | 114 | 109.5 | 82.5-158.5 |
| 2 | 41 | 78.4 | 47.4-138.6 |
| 3 | 58 | 69.9 | 44.4-176.5 |

Example 14

Alper-HER2 mAb (2HE) Detects Stomach Cancer Cells

Figure 7A:
FIGS. 7A, and 7B. Alper-HER2 mAb (2HE) stained cancer stomach cells
Figure 7B:

Alper-HER2 mAb 2HE detects HER2 in membranes from stomach cancer patients. See FIG. 7.

Example 15

Alper-HER2 mAb (2HE) Detects Colon Cancer Cells

Figure 8A:
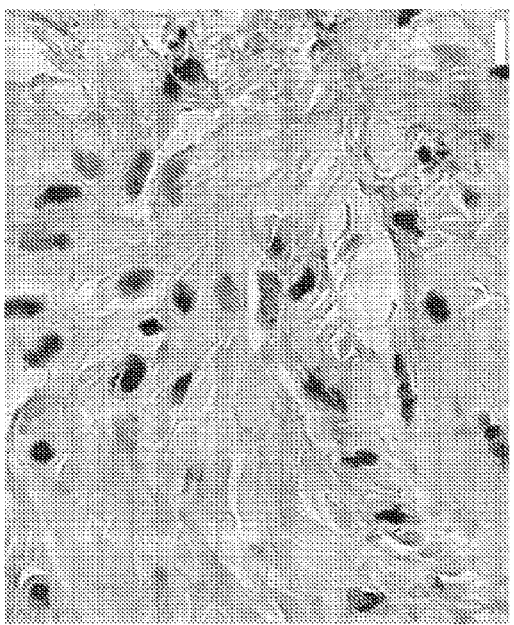
FIGS. 8A, 8B, and 8C. Alper-HER2 mAb (2HE) stained normal and cancer colon cells
Figure 8B:
Figure 8C:
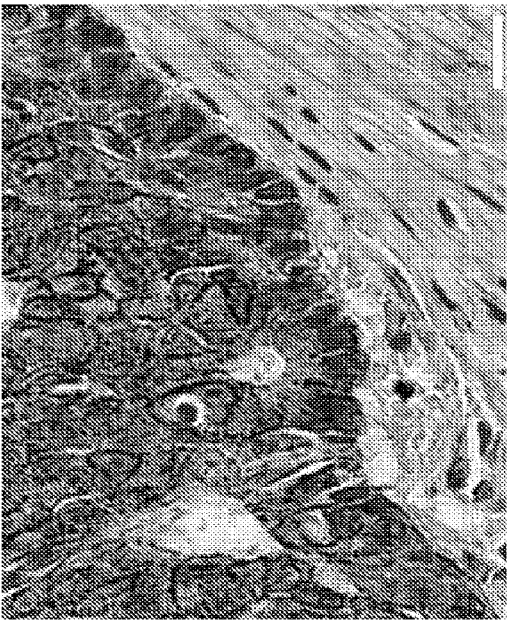

Alper-HER2 mAb 2HE detects HER2 in membranes of colon cancer patients, but not of normal control subjects. See FIG. 8.

What is claimed is:

1. A method of performing an immunoassay for a HER2 antigen in a biological sample, comprising: (a) contacting said biological sample with an antibody comprising a heavy chain variable domain comprising three complementarity determining regions (CDRs) comprising the amino acid sequences of SEQ ID NO: 2, SEQ ID NO:3, and SEQ ID NO:4, and a light chain variable domain comprising three CDRs comprising the amino acid sequences of SEQ ID NO: 6, Aspartic Acid-Threonine-Serine, and SEQ ID NO:7; and (b) qualitatively or quantitatively determining the formation of an immune complex of the antibody and the HER2 antigen.

2. The method of claim 1, wherein the biological sample comprises a human cancer cell selected from a breast, stomach, lung, and colon cancer cell.

3. The method of claim 1, wherein the heavy chain amino acid sequence of the antibody comprises the sequence of SEQ ID NO: 1 and the light chain amino acid sequence of the antibody comprises the sequence of SEQ ID NO: 5.

4. The method of claim 1, wherein the biological sample is chosen from a blood, serum, and plasma sample from a patient having cancer or in need of diagnosis thereof.

5. The method of claim 4, wherein the determining step comprises contacting an immune complex of the antibody and the HER2 antigen with a secondary antibody and quantitatively or qualitatively determining binding of the secondary antibody to the immune complex.

6. The method of claim 5, wherein the secondary antibody is fluorescently labeled.

7. The method of claim 1, wherein the biological sample is chosen from a blood, serum, and plasma sample from a patient having breast cancer or in need of diagnosis thereof.

8. The method of claim 1, wherein the immunoassay is an ELISA.

9. The method of claim 8, wherein the ELISA is performed on a biological sample chosen from tissue, blood, serum, and plasma.

10. The method of claim 9, wherein the biological sample is from a patient in need of diagnosis and a determination that the HER2 antigen is present in the biological sample indicates the presence of cancer in the patient.

11. The method of claim 9, wherein the biological sample is from a patient having breast, colon, or stomach cancer.

12. The method of claim 8, wherein the heavy chain amino acid sequence of the antibody comprises the sequence of SEQ ID NO: 1 and the light chain amino acid sequence of the antibody comprises the sequence of SEQ ID NO: 5.

13. The method of claim 8, wherein the ELISA is a sandwich assay.

14. The method of claim 13, wherein the sandwich assay is performed on a biological sample chosen from tissue, blood, serum, and plasma.

15. The method of claim 13, wherein the biological sample is from a patient in need of diagnosis, and a determination that the HER2 antigen is present in the biological sample indicates the presence of cancer in the patient.

16. The method of claim 13, wherein the heavy chain amino acid sequence of the antibody comprises the sequence of SEQ ID NO: 1 and the light chain amino acid sequence of the antibody comprises the sequence of SEQ ID NO: 5.

17. The method of claim 1, wherein the immunoassay is an immunohistochemical assay for the HER2 antigen, the biological sample is a breast cancer tissue sample, and the level of HER2 antigen detected correlates positively with expected patient survival time.

18. The method of claim 17, wherein the breast cancer tissue sample is from a nodal positive patient.

19. The method of claim 17, wherein the heavy chain amino acid sequence of the antibody comprises the sequence of SEQ ID NO: 1 and the light chain amino acid sequence of the antibody comprises the sequence of SEQ ID NO: 5.

20. The method of claim 1, wherein the sample is from a patient suffering from a disease characterized by the expression of a HER2 gene product.

* * * * *